(12) United States Patent
Regev et al.

(10) Patent No.: US 11,996,168 B2
(45) Date of Patent: May 28, 2024

(54) SYSTEMS AND METHODS FOR DETERMINING RELATIVE ABUNDANCES OF BIOMOLECULES

(71) Applicants: THE BROAD INSTITUTE, INC., Cambridge, MA (US); MASSACHUSETTS INSTITUTE OF TECHNOLOGY, Cambridge, MA (US)

(72) Inventors: Aviv Regev, Cambridge, MA (US); Eric S. Lander, Cambridge, MA (US); Brian Cleary, Cambridge, MA (US); Le Cong, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 877 days.

(21) Appl. No.: 15/771,981

(22) PCT Filed: Oct. 27, 2016

(86) PCT No.: PCT/US2016/059230
§ 371 (c)(1),
(2) Date: Apr. 27, 2018

(87) PCT Pub. No.: WO2017/075292
PCT Pub. Date: May 4, 2017

(65) Prior Publication Data
US 2018/0341744 A1 Nov. 29, 2018

Related U.S. Application Data

(60) Provisional application No. 62/372,393, filed on Aug. 9, 2016, provisional application No. 62/247,630, filed on Oct. 28, 2015.

(51) Int. Cl.
*G16B 25/10* (2019.01)
*G06N 7/01* (2023.01)
(Continued)

(52) U.S. Cl.
CPC ............... *G16B 25/10* (2019.02); *G06N 7/01* (2023.01); *G06N 20/00* (2019.01); *G06N 20/10* (2019.01);
(Continued)

(58) Field of Classification Search
CPC ........ C12Q 2563/179; C12Q 2537/143; C12Q 2565/514; C12Q 2600/16; C12Q 2537/165; C12Q 2600/166; C12Q 1/6869; C12Q 2600/106; C12Q 1/6806; C12Q 1/6874; C12Q 1/6844; C12Q 1/6813; C12Q 1/6876; C12Q 2500/00; C12Q 2520/00; C12Q 2560/00; C12Q 2563/107; C12Q 2565/501; C12Q 2565/513; C40B 70/00; C40B 20/04; G01N 33/6845; G01N 2458/10; G01N 33/5308; G01N 2800/60; G01N 33/48; G16B 20/00; G16B 30/00; G16B 99/00; G16B 20/20; G16B 20/40; G16B 25/00; G16B 30/10; G16B 30/20; G16B 40/00; G16B 50/00; G16B 50/30; G16B 50/50; G16B 25/10; G16B 5/00; G16B 40/20; G16B 25/20; G16B 25/30; G16B 35/10; G16B 35/20; G16H 50/20; G16H 50/30; G16H 10/60; G16H 50/70; G06K 2009/4695; G06K 9/4633; G06K 9/52;
(Continued)

(56) References Cited

U.S. PATENT DOCUMENTS 4,849,077 A  7/1989 Rosenthal
4,971,903 A  11/1990 Hyman
(Continued)

FOREIGN PATENT DOCUMENTS

WO  93/23564 A1  11/1993
WO  96/39154 A1  12/1996
(Continued)

OTHER PUBLICATIONS

Mohtashemi et al. (2011) Open-target sparse sensing of biological agents using DNA microarray. BMC bioinformatics 12:314. (11 pages) (Year: 2011).*
Slawski et al. (2014) Sparse recovery for protein mass spectrometry data. In Rish (ed) Practical applications of Sparse Modeling, MIT press, Chapter 5, p. 79-98. (Year: 2014).*
(Continued)

*Primary Examiner* — Mary K Zeman
(74) *Attorney, Agent, or Firm* — F. Brent Nix, Esq.; Johnson, Marcou, Isaacs & Nix, LLC; Drew P. Harding

(57) ABSTRACT

The present invention relates to genomic informatics and gene-expression profiling. Gene-expression profiles provide complex molecular fingerprints regarding the relative state of a cell or tissue. Similarities in gene-expression profiles between organic states provide molecular taxonomies, classification, and diagnostics. Similarities in gene-expression profiles resulting from various external perturbations reveal functional similarities between these perturbagens, of value in pathway and mechanism-of-action elucidation. Similarities in gene-expression profiles between organic and induced states may identify clinically-effective therapies. Systems and methods herein provide for the measurement of relative gene abundances, including unbiased selection of and construction of probes and targets designed and methods for using known properties of sparsity of measurements to reach gene abundances.

17 Claims, 25 Drawing Sheets

(51) Int. Cl.
| | |
|---|---|
| G06N 20/00 | (2019.01) |
| G06N 20/10 | (2019.01) |
| G16B 25/00 | (2019.01) |
| G16B 40/00 | (2019.01) |
| G16B 40/20 | (2019.01) |

(52) U.S. Cl.
CPC ............. *G16B 25/00* (2019.02); *G16B 40/00* (2019.02); *G16B 40/20* (2019.02)

(58) Field of Classification Search
CPC ............. G06K 9/6201; G06K 9/00523; G06K 9/6249; G06N 20/00; G06N 7/005; G06N 20/10; G06F 17/13; G06F 17/16; G06F 8/22; G06F 15/16; G06F 16/288; G06F 8/24; G06Q 10/04; C12N 15/1096; C12N 15/11; C12N 15/52; C12N 15/625; C12N 15/65; C12N 2310/10; C12N 2320/12; C12N 2320/13

See application file for complete search history.

(56) References Cited

U.S. PATENT DOCUMENTS

| | | | |
|---|---|---|---|
| 5,202,231 A | 4/1993 | Drmanac et al. | |
| 5,210,015 A | 5/1993 | Gelfand et al. | |
| 5,403,708 A | 4/1995 | Brennan et al. | |
| 5,445,934 A | 8/1995 | Fodor et al. | |
| 5,525,464 A | 6/1996 | Drmanac et al. | |
| 5,547,839 A | 8/1996 | Dower et al. | |
| 5,695,940 A | 12/1997 | Drmanac et al. | |
| 5,795,782 A | 8/1998 | Church et al. | |
| 5,902,723 A | 5/1999 | Dower et al. | |
| 2013/0090254 A1* | 4/2013 | Lamb ................... | C12Q 1/6809 702/20 |
| 2014/0106976 A1* | 4/2014 | Sachs ..................... | G01N 15/14 506/9 |
| 2014/0309122 A1* | 10/2014 | Min ....................... | G16B 40/00 506/8 |
| 2015/0294062 A1* | 10/2015 | Quon ..................... | G16B 20/00 702/19 |
| 2018/0082153 A1* | 3/2018 | Wan ....................... | G06T 7/0014 |
| 2018/0341744 A1 | 11/2018 | Regev et al. | |
| 2019/0085324 A1* | 3/2019 | Regev ..................... | G16B 5/00 |
| 2020/0152289 A1* | 5/2020 | Cleary ................... | G16B 50/50 |
| 2020/0362334 A1* | 11/2020 | Regev ................... | C12Q 1/6869 |

FOREIGN PATENT DOCUMENTS

| | | | |
|---|---|---|---|
| WO | 97/03211 A1 | 1/1997 | |
| WO | 98/13523 A1 | 4/1998 | |
| WO | 98/28440 A1 | 7/1998 | |
| WO | 2014/047556 A1 | 3/2014 | |
| WO | 2017075292 A1 | 5/2017 | |

OTHER PUBLICATIONS

Gleichman et al. (2011) Blind Compressed Sensing. IEEE transaction on information theory vol. 57 No. 10 p. 6958-6964. (Year: 2011).*

Tolliver et al. (2010) Robust unmixing of tumor states in array comparative genomic hybridization data. Bioinformatics vol. 26 i106-i114. (Year: 2010).*

Seeger, et al. (2007) Bayesian inference and optimal design in the sparse linear model. Proceedings of machine learning research. vol. 2:444-451. (Year: 2007).*

Cheng et al. (2015) Efficient sparse representation and modeling. In Cheng, (eds) Sparse representation, modeling and learning in visual recognition: theory, algorithms and applications. Chapter 5, p. 117-151. (Year: 2015).*

Duma, D. (2013) a combinatorial pooling strategy for the selective sequencing of very large and repetitive genomes. Thesis, UC Riverside. https://escholarship.org/uc/item/3xm8t5rg (Year: 2013).*

Parvaresh, F. et al. Recovering sparse signals using sparse measurement matrices in compressed DNA microarrays. IEEE Journal of selected topics in signal processing, vol. 2, No. 3 (2008) p. 275-285. (Year: 2008).*

Devarajan, K. Nonnegative matrix factorization: an analytical and interpretive tool in computational biology. PLOS Computational Biology 4:7 e1000029 (2008) 12 pages. (Year: 2008).*

Amir et al. Bacterial community reconstruction using compressed sensing. (2011) Journal of computational biology 18:11 pp. 1723-1741. (Year: 2011).*

Gliechman et al. 2011 IEEE transactions on information theory 57 10 2011, p. 6958 6075 (Year: 2011).*

Burczynski et al., "Molecular Classification of Crohn's Disease and Ulcerative Colitis Patients using Transcriptional Profiles in Peripheral Blood Mononuclear Cells", The Journal of Molecular Diagnostics, vol. 8, No. 1, Feb. 2006, 51-61.

Candes et al., "Compressive Sampling", Proceedings of the International Congress of Mathematicians Madrid, Aug. 22-30, 2006, 20 pages.

Datlinger et al., "Pooled CRISPR Screening with Single-Cell Transcriptome Read-Out", Nature Methods, vol. 14, No. 3, Mar. 2017, 20 pages.

Dramanac et al., "Sequencing of Megabase Plus DNA by Hybridization: Theory of the Method", Genomics, vol. 4, Issue 2, Feb. 1989, 114-128.

Sanger, et al., "DNA Sequencing with Chain-Terminating Inhibitors", Proceedings of the National Academy of Sciences, vol. 74, No. 12, Dec. 1977, 5463-5467.

Elgen et al., "Sorting Single Molecules: Application to Diagnostics and Evolutionary Biotechnology", Proceedings of the National Academy of Sciences of the United States of America, vol. 91, No. 13, Jun. 21, 1994, 5740-5747.

Glas et al., "Gene Expression Profiling in Follicular Lymphoma to Assess Clinical Aggressiveness and to Guide the Choice of Treatment", Blood, vol. 105, No. 1, Jan. 1, 2005, 301-307.

Golub et al., "Molecular Classification of Cancer: Class Discovery and Class Prediction by Gene Expression Monitoring", Science, vol. 286, No. 5439, Oct. 15, 1999, 531-537.

Hyman Edward, "A New Method of Sequencing DNA", Analytical Biochemistry, vol. 174, Issue 2, Nov. 1, 1988, 423-436.

Johnson et al., "Continuous Assay for DNA Polymerization by Light Scattering", Analytical Biochemistry, vol. 136, Issue 1, Jan. 1984, 192-194.

Jones, "An Iterative and Regenerative Method for DNA Sequencing", Biotechniques, vol. 22, No. 5, May 1997 938-946.

Koster et al., "A Strategy for Rapid and Efficient DNA Sequencing by Mass Spectrometry", Nature Biotechnology, vol. 14, No. 9, Sep. 1996, 1123-1128.

Lamb et al., "A Mechanism of Cyclin D1 Action Encoded in the Patterns of Gene Expression in Human Cancer", Cell, vol. 114, No. 3, Aug. 8, 2003, 323-334.

Lamb Justin, "The Connectivity Map: A New Tool for Biomedical Research", Nature Reviews Cancer, vol. 7, No. 1, Jan. 2007, 54-60.

Lamb et al., "The Connectivity Map: Using Gene-Expression Signatures to Connect Small Molecules, Genes, and Disease", Science, vol. 313, No. 5795, Sep. 29, 2006, 1929-1935.

Lee et al., "Efficient Sparse Coding Algorithms", Computer Science Department, Stanford University, Stanford, CA 94305, 2006, 8 pages.

Macosko et al., "Highly Parallel Genome-Wide Expression Profiling of Individual Cells Using Nanoliter Droplets", Cell, vol. 161, No. 5, May 21, 2015, 25 pages.

Metzker et al., "Termination of DNA Synthesis by Novel 3'-Modified-Deoxyribonucleoside 5'-Triphosphates", Nucleic Acids Research, vol. 22, No. 20, Oct. 1994, 4259-4267.

Nyren et al., "Enzymatic Method for Continuous Monitoring of Inorganic Pyrophosphate Synthesis", Analytical Biochemistry, vol. 151, No. 2, Dec. 1985, 504-509.

Ramaswamy et al., "Multiclass Cancer Diagnosis using Tumor Gene Expression Signatures", Proceedings of the National Academy of Sciences of the United States of America, vol. 98, No. 26, Dec. 18, 2001, 15149-15154.

(56) References Cited

OTHER PUBLICATIONS

Ronaghi et al., "A Sequencing Method Based on Real-Time Pyrophosphate", Science, vol. 281, No. 5375, Jul. 17, 1998, 5 pages.
Ronaghi et al., "Real-Time DNA Sequencing Using Detection of Pyrophosphate Release", Analytical Biochemistry, vol. 242, No. 1, Nov. 1996, 84-89.
Vijver et al., "A Gene-Expression Signature as a Predictor of Survival in Breast Cancer", The New England Journal of Medicine, vol. 347, No. 25, Dec. 19, 2002, 1999-2009.
"International Preliminary Report on Patentability_for_PCT_Application_No_PCT_US2016_059230_", dated May 11, 2018, 1-15.
Young, "International Search Report and Written Opinion issued in International Application No. PCT/US2016/059230,", dated Feb. 16, 2017, 10 pages.

\* cited by examiner

SYSTEMS AND METHODS FOR DETERMINING RELATIVE ABUNDANCES OF BIOMOLECULES

CROSS-REFERENCE TO RELATED APPLICATIONS

This application is the U.S. National Stage of International Application No. PCT/US2016/059230, filed Oct. 27, 2016, which claims the benefit of U.S. Provisional Application No. 62/247,630, filed Oct. 28, 2015, and U.S. Provisional Application No. 62/372,393, filed Aug. 9, 2016. The entire contents of the above-identified priority applications are hereby fully incorporated herein by reference.

STATEMENT REGARDING FEDERALLY SPONSORED RESEARCH

This invention was made with government support under Grant Nos. HG006193 and M105960 awarded by the National Institutes of Health. The government has certain rights in the invention. The government has certain rights in the invention.

TECHNICAL FIELD

The subject matter disclosed herein is generally directed to systems and methods for the measurement of relative gene abundances, including unbiased selection of and construction of probes and targets designed and methods for using known properties of sparsity of measurements to reach gene abundances.

BACKGROUND

High-density, whole-transcriptome DNA microarrays are the method of choice for unbiased gene-expression profiling. These profiles have been found useful for the classification and diagnosis of disease, predicting patient response to therapy, exploring biological mechanisms, in classifying and elucidating the mechanisms-of-action of small molecules, and in identifying new therapeutics: Van de Vijver et al., "A gene expression signature as a predictor of survival in breast cancer" N Engl J Med 347:1999-2009 (2002); Lamb et al., "A mechanism of cyclin D1 action encoded in the patterns of gene expression in human cancer" Cell 114:323-334 (2003); Glas et al., "Gene expression profiling in follicular lymphoma to assess clinical aggressiveness and to guide the choice of treatment" Blood 105:301-307 (2005); Burczynski et al., "Molecular classification of Crohn's disease and ulcerative colitis patients using transcriptional profiles in peripheral blood mononuclear cells" J Mol Diagn 8:51-61 (2006); Golub et al., "Molecular classification of cancer: class discovery and class prediction by gene expression monitoring" Science 286:531 (1999); Ramaswamy et al., "Multiclass cancer diagnosis using tumor gene expression signatures" Proc Natl Acad Sci 98:15149 (2001); Lamb et al., "The Connectivity Map: using gene-expression signatures to connect small molecules, genes and disease" Science 313:1929 (2006). However, the overall success and wide-spread use of these methods is severely limited by the high cost and low throughput of existing transcriptome-analysis technologies. For example, using gene-expression profiling to screen for small molecules with desirable biological effects is practical only if one could analyze thousands of compounds per day at a cost dramatically below that of conventional microarrays.

Citation or identification of any document in this application is not an admission that such document is available as prior art to the present invention.

SUMMARY

A simple, flexible, and cost-effective, transcriptome-wide gene-expression profiling solution that does not require measuring individual genes or single cell profiling is desired. This would greatly accelerate the rate of discovery of medically-relevant connections encoded therein by leveraging knowledge of relative abundances of genes to extrapolate underlying cell circuitry.

The present invention relates to genomic informatics and gene-expression profiling. Gene-expression profiles provide complex molecular fingerprints regarding the relative state of a cell or tissue. Similarities in gene-expression profiles between organic states (i.e., for example, normal and diseased cells and/or tissues) provide molecular taxonomies, classification, and diagnostics. Similarities in gene-expression profiles resulting from various external perturbations (i.e., for example, ablation or enforced expression of specific genes, and/or small molecules, and/or environmental changes) reveal functional similarities between these perturbagens, of value in pathway and mechanism-of-action elucidation. Similarities in gene-expression profiles between organic (e.g. disease) and induced (e.g. by small molecule) states may identify clinically-effective therapies.

To achieve these and other advances and in accordance with the purpose of the present invention, as embodied and broadly described, in one aspect of the present invention, a probe set comprising 100 or more molecules assembled according to a set of random measurement values forming at least one measurement vector, where each molecule comprises a tag for the at least one measurement vector operably linked to a probe for one type of transcript of a plurality of types of transcripts.

In an aspect of the present invention, the probe set corresponds to a Design Matrix comprising m×n measurement values, where m is a number of measurement vectors and n is the number of types of transcripts. In another aspect, the tag uniquely corresponds to one of the measurement vectors. In an aspect, the molecules of the probe set are single-stranded DNA. In an aspect, the tag is a barcode. In another aspect, the transcript is a gene.

In an aspect, the number of measurement vectors is approximately 100-30,000. In an aspect, the number of measurement vectors is based on an estimate of system sparsity. In an aspect, the number of measurement vectors is based on the log of the number of types of transcripts. In an aspect the number of measurement vectors is approximately k log (n), where k is an estimate of sparsity. In an aspect, the Design Matrix may be adjusted according to a basis. In an aspect, k is approximately equal to 10. In another aspect, m is less than n. In another aspect, n is greater than 10.

In another aspect of the invention, a method of measuring relative abundances of transcripts in a pool of samples, comprises generating a Design Matrix comprising m×n measurement values, where m is a number of measurement vectors and n is the number of types of transcripts; generating a probe library corresponding to the Design Matrix, wherein the probe library comprises a collection of molecules assembled according to the measurement values, where each molecule has a tag for one of the measurement vectors operably linked to a probe for one of the types of transcripts; contacting the probe library to the pool of samples, resulting in m measurement results for each sample of the pool of samples; generating an Observed Measurement Matrix M comprising the measurement results for each sample of the pool of samples; and applying a sparse coding solving process to the Observed Measurement Matrix M to learn system matrix S as indicative of relative abundance of the transcripts in each of the samples.

In another aspect of the present invention, the measurement values in the Design Matrix are independent. In another aspect, the measurement values in the Design Matrix are random.

In an aspect, the number of measurement vectors is approximately 100-30,000. In an aspect, the number of measurement vectors is based on an estimate of system sparsity. In an aspect, the number of measurement vectors is based on the log of the number of types of transcripts. In an aspect the number of measurement vectors is approximately k log (n), where k is an estimate of sparsity. In an aspect, the Design Matrix may be adjusted according to a basis. In an aspect, k is approximately equal to 10. In another aspect, m is less than n. In another aspect, n is greater than 10.

In another aspect of the present invention, the tag uniquely corresponds to one of the measurement vectors. In an aspect, the tag is a barcode.

In another aspect of the present invention, the molecules of the probe library are single-stranded DNA. In an aspect, each molecule in the probe library further comprises a tag for one of the samples.

In another aspect of the present invention, the contacting includes binding and the contacting may, in some aspects, include hybridization.

In another aspect of the present invention, the sample is a cell.

In another aspect of the present invention, generating the Observed Measurement Matrix include hybrid selection and tag quantification. In an aspect, tag quantification includes sequencing.

In another aspect of the present invention, a method for measuring relative abundances of n biomolecules in a pool of samples, comprises generating a Design Matrix comprising m×n measurement values, where m is a number of measurement vectors and n is the number of types of biomolecules; generating a probe library corresponding to the Design Matrix, wherein the probe library comprises a collection of molecules assembled according to the measurement values, where each molecule has a tag for one of the measurement vectors operably linked to a probe for one of the types of biomolecules; contacting the probe library to the pool of samples, resulting in m measurement results for each sample of the pool of samples; generating an Observed Measurement Matrix M comprising the measurements results for each sample in the pool of samples; and applying a sparse coding solving process to the Observed Measurement Matrix to learn system matrix S as indicative of relative abundance of the biomolecules in each of the samples.

In another aspect of the present invention, the measurement values in the Design Matrix are independent. In another aspect, the measurement values in the Design Matrix are random.

In an aspect of the present invention, the biomolecule is a transcript, protein, DNA, non-naturally occurring nucleic acid, peptide. In an aspect of the present invention, the samples include cells, blood, hair, nails, mucus, tissue, feces or urine. In an aspect of the present invention, the probe is a molecule that binds to the biomolecule. In an aspect, the probe is a complex of molecules. In another aspect, the probe comprises an antibody or binding fragment thereof.

In another aspect of the present invention, the molecules of the probe library are single-stranded DNA. In an aspect, each molecule in the probe library further comprises a tag for one of the samples.

In another aspect of the present invention, the contacting includes binding and the contacting may, in some aspects, include hybridization.

In another aspect of the present invention, the tag uniquely corresponds to one of the measurement vectors. In an aspect, the tag is a barcode. In an aspect, each molecule in the probe library further comprises a tag for one of the samples.

In an aspect, the number of measurement vectors is approximately 1-30,000. In an aspect, the number of measurement vectors is based on an estimate of system sparsity. In an aspect, the number of measurement vectors is based on the log of the number of types of biomolecules. In an aspect the number of measurement vectors is approximately k log (n), where k is an estimate of sparsity. In an aspect, the Design Matrix may be adjusted according to a basis. In an aspect, k is approximately equal to 10. In another aspect, m is less than n. In another aspect, n is greater than 10.

In another aspect of the present invention, generating the Observed Measurement Matrix include tag quantification. In an aspect, tag quantification includes sequencing.

In an aspect of the present invention, the sparse coding solving process comprises the use of noisy compositional observations.

In an aspect of the present invention, the sparse coding solving process comprises a matrix factorization step. In an aspect, the matrix factorization step comprises non-negative matrix factorization (NMF). In another aspect, the matrix factorization step comprises sparse module activity factorization (SMAF).

In an aspect of the present invention, the sparse coding solving process comprises compressed sensing (CS) using training data to learn the system matrix S. In another aspect of the present invention, the sparse coding solving process comprises blind compressed sensing (BCS) to learn the system matrix S.

In an aspect of the present invention, the sparse coding solving process comprises sparse module activity factorization (SMAF) for the matrix factorization step and blind compressed sensing (BCS) to learn the system matrix S.

In another aspect, the methods disclosed herein are applied to measuring n biomolecules in single cells.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 25 illustrates an embodiment of distributional measurements made by annealing, ligation, and index primer amplification.

Figure 1:
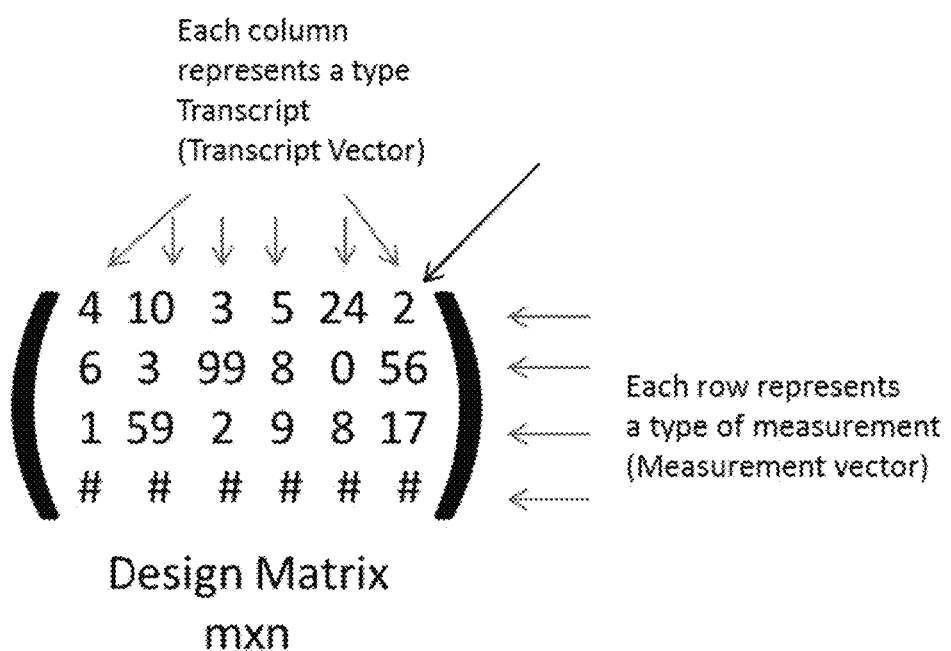
FIG. 1 is an illustrative example of a Design Matrix according to aspects of the present invention.
Figure 2:
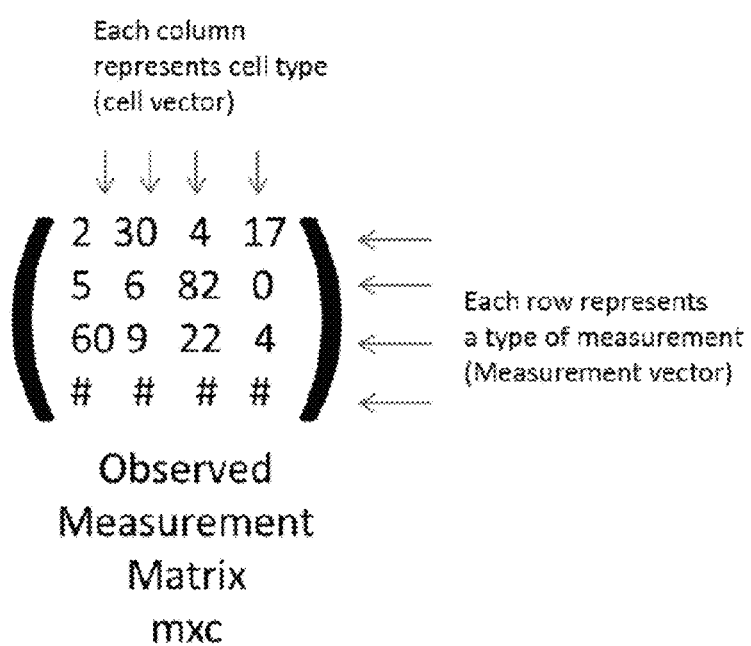
FIG. 2 is an illustrative example of an Observed Measurement Matrix according to aspects of the present invention.

The patent or application file contains at least one drawing executed in color. Copies of this patent or patent application publication with color drawing(s) may be provided by the Office upon request and payment of the necessary fee.

DETAILED DESCRIPTION OF THE EXAMPLE EMBODIMENTS

Overview

The term "device" as used herein, refers to any composition capable of measuring expression levels of transcripts. For example, a device may comprise a solid planar substrate capable of attaching nucleic acids (i.e., an oligonucleotide microarray). Alternatively, a device may comprise a solution-based bead array, wherein nucleic acids are attached to beads and detected using a flow cytometer. Alternatively, a device may comprise a nucleic-acid sequencer.

The term "probe" as used herein, refers to any molecule capable of attaching and/or binding or hybridizing to a nucleic acid. A probe may be a nucleic acid probe, such as a polynucleotide probe, or such as an oligonucleotide probe. A probe may be a DNA probe or an RNA probe, preferably a DNA probe. A nucleic acid probe typically has sufficient complementarity to its target in order to specifically or exclusively bind to or hybridize to said target. Suitable hybridization conditions are known in the art. For example, a capture probe may be an oligonucleotide attached or attachable to a bead, wherein the oligonucleotide is at least partially complementary to another oligonucleotide. Alternatively, a capture probe may comprise a polyethylene glycol linker, an antibody, a polyclonal antibody, a monoclonal antibody, an Fab fragment, a biological receptor complex, an enzyme, a hormone, an antigen, and/or a fragment or portion thereof. A probe may be a nucleic acid sequence, the nucleic acid being for example deoxyribonucleic acid (DNA), ribonucleic acid (RNA), peptide nucleic acid (PNA) or other non-naturally occurring nucleic acid.

A probe (e.g., an oligonucleotide probe) as described herein may be composed of or may comprise two probe halves or segments, a left probe and a right probe (or a 5' probe and a 3' probe, respectively). Each half or segment comprises at least a target specific hybridization portion. The left probe may have a 3' target specific nucleotide sequence (i.e. hybridization portion). The right probe may have a 5' target specific nucleotide sequence (i.e. hybridization portion). The hybridization portions of left and right probe halves may be chosen such that directly juxtaposed target sequences are hybridized therewith. Upon hybridization of the target sequence of the left and right probes, the two probe halves or segments may be ligated to each other, providing for a common or single molecule (e.g., an oligonucleotide) comprising both probe halves (termed herein "reconstituted probe" for convenience). If the target sequence is DNA (e.g., cDNA) and the probes are DNA, any suitable DNA ligase may be used to this end. If the target sequence is RNA (e.g., mRNA) and the probes are DNA, a DNA ligase which recognizes DNA:RNA hybrids may be used to ligate both probe halves. Suitable DNA ligases for DNA:RNA hybrids are for instance T4 DNA ligase (optionally with K159A mutation) or DNA ligase as described in Lohman et al. (2013) "Efficient DNA ligation in DNA-RNA hybrid helices by *Chlorella* virus DNA ligase"; Nucleic Acid Research; doi: 10.1093/nar/gkt1032; commercially available by NEB as SplintR® ligase.

The probes (e.g., any one or both probe halves or segments) may be labeled and/or may be provided with adapter sequences (which do not bind to the target sequence). Adapter sequences may comprise, consist essentially of or consist of primer binding sequences which allow amplification and/or sequencing of the reconstituted probe (i.e., the ligated left and right probe halves or segments). The left and right probes may comprise the same of different adapter sequences (or sections of the adapter sequence). Each (reconstituted) probe may comprise the same or different adapter sequences (or sections of the adapter sequence). Each probe in a particular pool of probes may comprise the same adapter sequence (or sections of the adapter sequence). Different pools of probes (or probes from different pools of probes) may comprise different adapter sequences (or sections of the adapter sequence). Hence, in certain embodiments, reconstituted probes produced by hybridization of the various probes included in a given probe pool (each composed of or comprising two probe halves) to their respective target sequences and subsequent ligation of the probe halves, can be amplified using a common primer pair directed to (i.e., binding to/complementary to) the common adapter sequences included in the probes. Hereby, the amplification product can be quantified, providing for a single quantitative readout value for the pool. In certain embodiments, separate amplification reactions may be performed for distinct pools. In other embodiments, a common amplification reaction may be performed for two or more or all pools in accordance with the well-known practice of multiplexing, still allowing for separate readouts of the amplification products for each pool.

Figure 13:
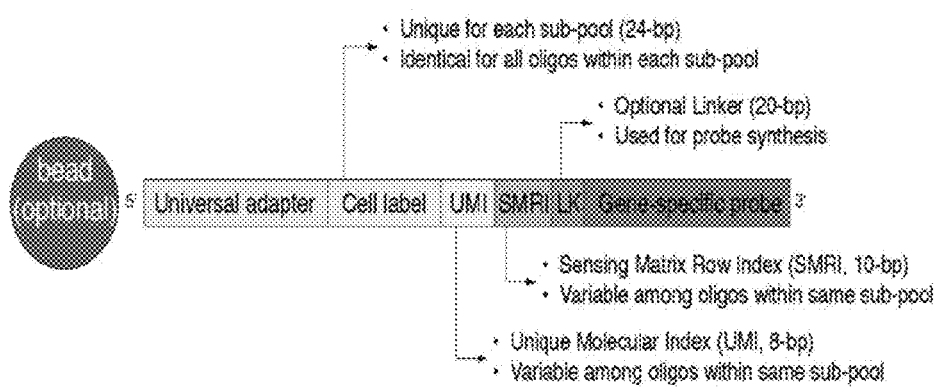
FIG. 13 illustrates the probe design, specifically the left side of the probe only.
Figure 14A:
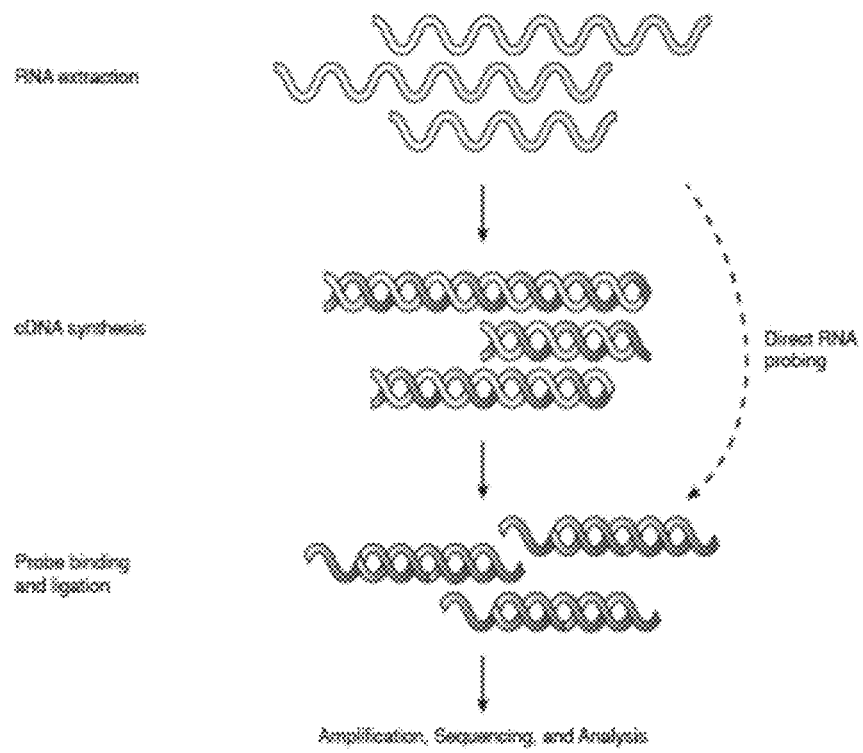
FIG. 14A illustrate a schematic of the experimental implementation.
Figure 14B:
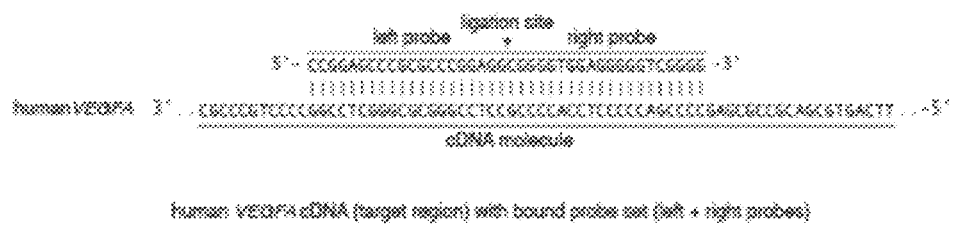
FIG. 14B displays left and right (or 5' and 3') probe sides may bind cDNA or alternatively (shown as "Direct RNA probing) may bind RNA, e.g., mRNA, directly.

As described herein elsewhere, the probes (left probe, right probe, or reconstituted probe) may further comprise one or more additional sequences as or within the adapter sequences, such as linker sequences, and/or identifier or index sequences, such as UMI sequences or other identifier sequences allowing identification of individual probes or particular pools of probes (such as for instance described in an embodiment in FIG. 13). It will be understood that if a UMI is present in the probes, a different UMI may be present in each probe, whereas the same or a different primer binding sequence may be present on different probes (or probe pools).

Expression readout of the probes may involve amplification of the probes or subsets of the probes and may involve universal amplification or index-specific amplification. Index-specific amplification allows certain subsets of probes (up to individual probes) to be specifically amplified. Expression readout of the probes (or pools of probes) may be any means known in the art, including sequencing, quantitative PCR (qPCR), mass cytometry (CyTOF), etc. CyTOF is similar to traditional flow cytometry, with the modification that antibodies (or in situ hybridization probes) are conjugated to heavy metal ions rather than fluorophores. Readout may be done by time-of-flight mass spectrometry with a fixed number of channels corresponding to ~100 heavy metal ions. Since the number of channels is fundamentally limited, applying compressed sensing to expand the panel of targets by an order of magnitude or more could be transformative for this burgeoning technology.

The term "Design Matrix" as used herein, refers to a collection of the relative number of times up to which a type of transcript can be counted for a specific type of measurement. The collection may be described as a table and will be so in the following for the sake of the description. However, it is understood that the collection need not be generated as a table but can also be generated in any other form suitable for the measuring relative abundances of transcripts, e.g. a string of data. Each entry in the table is intended to be a randomly generated number, at least initially. In general, each row in the matrix corresponds to a specific type of measurement, while each column in the matrix corresponds to a type of transcripts in the sample pool. Thus, the number of rows in the Design Matrix corresponds to the number of specific types of measurements, while the number of columns in the Design Matrix corresponds to the number of types of transcripts in the sample pool. Of course, one of skill may choose to adjust the Design Matrix to reflect fewer than all available types of measurement and fewer than all types of transcripts in the sample pool. Further, one of skill in the art will appreciate that the Design Matrix itself may be transposed such that the number of rows indicates the number of types of transcripts, while the number of columns indicates the number of types of measurement.

The term "relative number of times" as used herein, means that if for a type of measurements, the relative number is $a_1$ for type of transcripts 1, $a_2$ for type of transcripts 2, . . . $a_n$ for type of transcripts n, then type of transcripts 1 can be counted up to $k.a_1$ times, type of transcripts 2 up to $k.a_2$ times, . . . type of transcripts n up to $k.a_n$ times; k being an integer.

The term "count" and its derivatives as used in the definitions, encompasses any method that yield a measured value indicative of the count.

The term "Observed Measurement Matrix" as used herein, refers to a collection of measured values of a specific type of measurement for a specific type of sample in the sample pool or portion of sample (such as a cell, or a type of cell). The collection may be described as a table and will be so in the following for the sake of the description. However, it is understood that the collection need not be generated as a table but can also be generated in any other form suitable for the measuring relative abundances of transcripts, e.g. a string of data. In general, each row in the matrix corresponds to a specific type of measurement, while each column in the matrix corresponds to a type of samples in the sample pool or portion of sample. Thus, the number of rows in the Observed Measurement Matrix corresponds to the number of specific types of measurements, while the number of columns in the Observed Measurement Matrix corresponds to the number of types of samples in the sample pool. Of course, one of skill may choose to adjust the Observed Measurement Matrix to reflect fewer than all available types of measurement and fewer than all types of samples in the sample pool. Further, one of skill in the art will appreciate that the Observed Measurement Matrix itself may be transposed such that the number of rows indicates the number of types of sample, while the number of columns indicates the number of types of measurement.

Correspondingly, any reference to a Matrix used herein, refers to a collection of values, which may be described as a table and will be so in the following for the sake of the description. However, it is understood that the collection need not be generated as a table but can also be generated in any other form suitable for the measuring relative abundances of transcripts, e.g. a string of data. Any reference to a vector (in the mathematical sense) used herein, refers to a collection of values which may be described as row or a column, in some instances row or column of a table, and will be so in the following for the sake of the description. However, it is understood that the collection need not be generated as a row or a column but can also be generated in any other form suitable for the measuring relative abundances of transcripts.

The term "Connectivity Map" as used herein, refers to a public database of transcriptome-wide gene-expression profiles derived from cultured human cells treated with a plurality of perturbagens, and pattern-matching algorithms for the scoring and identification of significant similarities between those profiles and external gene-expression data, as described by Lamb et al., "The Connectivity Map: using gene-expression signatures to connect small molecules, genes and disease". Science 313:1929 (2006). Build02 of the Connectivity Map contains 7,056 full-transcriptome gene-expression profiles generated with Affymetrix high-density oligonucleotide microarrays representing the biological effects of 1,309 small-molecule perturbagens, and is available at broadinstitute.org/cmap.

The term "query signature" as used herein, refers to any set of up- and down-regulated genes between two cellular states (e.g., cells treated with a small molecule versus cells treated with the vehicle in which the small molecule is dissolved) derived from a gene-expression profile that is suitable to query Connectivity Map. For example, a 'query signature' may comprise a list of genes differentially expressed in a distinction of interest; (e.g., disease versus normal), as opposed to an "expression profile" that illustrates all genes with their respective expression levels.

The term "connectivity score" as used herein, refers to a relative measure of the similarity of the biological effects of a perturbagen used to generate a query signature with those of a perturbagen represented in the Connectivity Map based upon the gene-expression profile of a single treatment with that perturbagen. For example, one would expect every treatment instances with vorinostat, a known histone deacetylase (HDAC) inhibitor, to have a high connectivity score with a query signature generated from the effects of treatments with a panel of HDAC inhibitors.

The term "enrichment score" as used herein, refers to a measure of the similarity of the biological effects of a perturbagen used to generate a query signature with those of a perturbagen represented in the Connectivity Map based upon the gene-expression profiles of multiple independent treatments with that perturbagen.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The sample may be a biological sample, for example a blood, buccal, cell, cerebrospinal fluid, mucus, saliva, semen, tissue, tumor, feces, urine, and vaginal sample. It may be obtained from an animal, a plant or a fungus. The animal may be a mammal. The rnammal may be a primate. The primate may be a human. In other embodiments, the sample may be an environmental sample, such as water or soil.

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Target sequence" is intended to designate either one target sequence or more than one target sequence, i.e. any sequence of interest at which the analysis is aimed. Thus, the sample may comprise more than one target sequence and preferably a plurality of target sequences, the number of which may be 2, 3, 4, 5, 6, 7, 8, 9, 10, 11, 12, 13, 14, 15, 16, 17, 18, 19, 20 and above. A target sequence may be comprised in a gene or gene transcript, such as gene mRNA.

The present invention is related to the field of genomic informatics and gene-expression profiling. Gene-expression profiles provide complex molecular fingerprints regarding the relative state of a cell or tissue. Similarities in gene-expression profiles between organic states (i.e., for example, normal and diseased cells and/or tissues) provide molecular taxonomies, classification, and diagnostics. Similarities in gene-expression profiles resulting from various external perturbations (i.e., for example, ablation or enforced expression of specific genes, and/or small molecules, and/or environmental changes) reveal functional similarities between these perturbagens, of value in pathway and mechanism-of-action elucidation. Similarities in gene-expression profiles between organic (e.g. disease) and induced (e.g. by small molecule) states may identify clinically-effective therapies. Improvements described herein allow for the efficient and economical generation of full-transcriptome gene-expression profiles by identifying cluster centroid landmark transcripts that predict the expression levels of other transcripts within the same cluster.

Some embodiments of the present invention contemplate measuring relative gene abundances of transcripts in a pool of samples to allow genome-wide transcriptional profiling for applications including, but not limited to, disease classification and diagnosis without resort to expensive and laborious microarray technology (i.e., for example, Affymetrix GeneChip microarrays). Other uses include, but are not limited to, generating gene-expression data for use in and with information databases (i.e., for example, connectivity maps). A connectivity map typically may comprise a collection of a large number of gene-expression profiles together with allied pattern-matching software. The collection of profiles is searched with the pattern-matching algorithm for profiles that are similar to gene-expression data derived from a biological state of interest. The utility of this searching and pattern-matching exercise resides in the belief that similar biological states may be identified through the transitory feature of common gene-expression changes. The gene-expression profiles in a connectivity map may be derived from known cellular states, or cells or tissues treated with known chemical or genetic perturbagens. In this mode, the connectivity map is a tool for the functional annotation of the biological state of interest. Alternatively, the connectivity map is populated with gene-expression profiles from cells or tissues treated with previously uncharacterized or novel perturbagens. In this mode, the connectivity map functions as a screening tool. Most often, a connectivity map is populated with profiles of both types. Connectivity maps, in general, establish biologically-relevant connections between disease states, gene-product function, and small-molecule action. In particular, connectivity maps have wide-ranging applications including, but not limited to, functional annotation of unknown genes and biological states, identification of the mode of action or functional class of a small molecule, and the identification of perturbagens that modulate or reverse a disease state towards therapeutic advantage as potential drugs. See Lamb et al, "The Connectivity Map: using gene-expression signatures to connect small molecules, genes and disease" Science 313: 1929-1935 (2006), and Lamb, "The Connectivity Map: a new tool for biomedical research" Nature Reviews Cancer 7: 54-60 (2007). However, the high cost of generating gene-expression profiles severely limits the size and scope of connectivity maps. A connectivity map populated with gene-expression profiles derived from every member of an industrial small-molecule drug-screening library, a saturated combinatorial or diversity-orientated chemical library, a comprehensive collection of crude or purified plant or animal extracts, or from the genetic ablation or forced expression of every gene in a mammalian genome, for example, would be expected to facilitate more, and more profound, biological discoveries than those of existing connectivity maps.

The present invention contemplates compositions and methods for making and using a transcriptome-wide gene-expression profiling platform that "under samples" the total number of transcripts. Because gene expression is believed to be highly correlated, direct measurement of a small number allows the expression levels of the remainder to be inferred. The present invention, therefore, has the potential to reduce the cost and increase the throughput of full-transcriptome gene-expression profiling relative to the well-known conventional approaches that require all transcripts to be measured.

Gene expression data are highly structured, such that the expression level of some genes is predictive of the expression level of others. Knowledge that gene expression data are highly structured allows for the assumption that the number of degrees of freedom in the system are small, which allows for assuming that the basis for computation of the relative gene abundances is sparse.

It is possible to make several biologically motivated assumptions that allow Applicants to recover the nonlinear interaction terms while under-sampling without having any specific knowledge of which genes are likely to interact. In particular, if Applicants assume that genetic interactions are low rank, sparse, or a combination of these, then the true number of degrees of freedom is small relative to the complete combinatorial expansion, which enables Applicants to infer the full nonlinear landscape with a relatively small number of perturbations. Working around these assumptions, analytical theories of matrix completion and compressed sensing may be used to design under-sampled combinatorial perturbation experiments. In addition, a kernel-learning framework may be used to employ under-sampling by building predictive functions of combinatorial perturbations without directly learning any individual interaction coefficient.

In the framework of matrix completion, or more generally tensor completion, the goal is to fill in all the values of a matrix using a small collection of sampled entries. Applicants hypothesize that the rank of a matrix of second-order interactions, or tensor of higher-order interactions, is a fraction of the number of genes being tested. Applicants can test this idea by explicitly calculating the rank from a dense sampling of second or third order knockouts from a small collection of genes. If the rank of interactions is indeed limited, then Applicants can randomly sample pairs of genes to knockout from a larger collection (in the second order case), and then fill in the remaining values via nuclear norm regularized least-squares optimization [Matrix Completion with Noise. E. Candes and Y. Plan]. Provable guarantees for this recovery suggest that if the rank r is small relative to the number of genes, n, then m samples such that $$m \geq O\left(\frac{6}{5} nr\log(n)\right)$$

are sufficient. However, these guarantees assume rough uniformity in the loadings of interaction singular vectors, and this assumption is unlikely to hold up if the interaction matrix itself is very sparse. In this case, Applicants can perform the same random sampling scheme, and then simultaneously regularize over both the nuclear norm, and $L^1$ norm of the interaction matrix [Estimation of Simultaneously Sparse and Low Rank Matrices. Richard et. al.]. As may be appreciated by one of skill in the art, the "sparsity" of a matrix is a measure of the non-zero elements of a matrix relative to the total number of elements of a matrix. A sparse matrix is a matrix in which most of the elements are zero, which is indicative of loose correlation between systems.

As may be appreciated by one of skill in the art, the "rank" of a matrix is the maximum number of linearly independent row vectors in the matrix or the maximum number of linearly independent column vectors in the matrix. The rank of a matrix denotes the "information content of the matrix. The lower the rank, the lower is the information content. A basis for a vector space is a collection of vectors that form a set that is linearly independent and that spans the space.

In the related setting of compressed sensing Applicants can directly leverage the sparse nature of interactions. In this case, instead of working with a tensor of interaction terms, Applicants work with a basis that spans all higher order interactions. This can be, for example, the Fourier basis of higher-order polynomials, in which case Applicants assume that there is a small number, s, of nonzero Fourier coefficients, which are not known a priori, but can accurately capture the effects of any combinatorial perturbation. Then, if Applicants make m random combinatorial knockouts, where m≥O(s log f) and f is the magnitude of combinatorial expansion (e.g.

$$\left(\text{e.g. } f = \binom{100}{3} = \text{"100 choose 3"} = 161700\right),$$

Applicants can recover the nonzero coefficients, and, thus, the set of nonlinear interaction terms, through $L^1$ regularized regression. Compressed sensing tells Applicants that if the perturbations are de-coherent under the given basis, then exact recovery is possible with dramatic under-sampling (in the noiseless case) [Compressive sampling. E. Candes.]. Applicants use this measure of de-coherence, then, as a guide in designing combinatorial perturbations. In particular, if each of m experiments includes a Poisson random sampling of knockouts, then Applicants expect the measurements to have good de-coherence under the Fourier basis, provided the mean number of knockouts is not too low (e.g. >1).

The formulations for matrix completion and compressed sensing each rely on a degree of sparsity—either in the rank or in the coefficients—to achieve recovery with under-sampling. For each of these Applicants can estimate the level of sparsity by performing dense combinatorial perturbations on a small collection of genes, or, in the case of compressed sensing, simply randomly sampling higher-order knockouts. However, Applicants also consider the alternative formulation of kernel learning, which does not have such strict demands on sparsity. In this case Applicants build predictive functions of the effects of combinatorial perturbations using a kernel of experimental similarity. More specifically, assume m experiments with Poisson random sampling of knockouts for each measurement. Then, Applicants can define an m-by-m polynomial kernel, for example, based on the overlap in knockouts between any pair of experiments. If Applicants build such a kernel, and learn the weighted combination of kernel vectors that fits a collection of training data, Applicants can then use these coefficients to predict the outcome of new experiments. In this case the density of nonlinear interaction terms can be much greater, since Applicants do not directly learn any particular interaction coefficient, but rather a kernelized version of the entire polynomial. In fact, if the interaction terms are too sparse, the kernel learning framework is unlikely to be successful with any significant under-sampling. However, together, kernel learning, matrix completion, and compressed sensing represent a complimentary range of approaches for inferring the effects of higher-order, combinatorial perturbations, with different assumptions on the underlying structure of the data for each framework.

The overall sparsity level of biological networks has been estimated in several ways. By comparing colony sizes between single and double mutants, the genetic landscape of *S. cerevisiae* has been mapped revealing that <5% of 5.4 million gene pairs interact significantly with respect to fitness. [Costanzo*, Baryshnikova* et. al., 2011] In mammalian cells, a systematic screen for ricin toxicity using a hierarchical approach revealed that among 60 genes with significant individual effects, interactions broadly divided genes into functional complexes and were of a relatively higher density [Bassik et. al., 2013]. A higher dimensional phenotype using imaging between 282 target genes, 20 query genes, and 11 phenotypes found approximately 5,000 significant interactions [Laufer et. al., 2013]. Sparsity with respect to gene expression phenotypes has not been well studied.

The empirical limits on the number of DSB that might be tenable for an individual cell to survive vary, but rough estimates using imaging of phosphorylation of H2AX and 53BP1 suggest this number could be in the 10-50 range.

According to embodiments of the present invention, each measurement integrates signal across many genes (for example, all 29k genes). Thus, the measurements are not sensitive to the stochastic capture of any single gene, but rather to the average signal across a broad range of genes. In this sense the present scheme is robust to technical noise. In addition, probe sets according to the present invention can be designed independently from any existing data. The probes are, in this sense, universally appropriate for any system desired to be measured. This method recognizes that there may be many different signature gene networks across many cell types/tissues, but that these are used to a sparse degree in any single cell. That is, in a single cell the number of active gene networks is small relative to the total number of all existing gene networks. This assumption can be used to under sample the transcriptome, such that a computational analysis is designed to recover signal from sparse systems. It is assumed that the gene networks (or their abstracted analogs) are sparsely used in any single cell, and specific knowledge of when the networks are active, or even the definitions of the networks themselves, are not required. Every gene is represented in every measurement, even if exact correlations between measurements, genes or expressions are not known. By analyzing transcriptomic measurements across many cells or tissues, it is possible to identify structures in the data that reflect the underlying cell circuitry. These same structures can be exploited to recover gene abundances, while dramatically under-sampling the full signal. In particular, if a given cell or tissue has a sparse representation in some basis, then Applicants can use the theories of compressive sensing and sparse coding to guide the design of RNA probe libraries that Applicants believe reduces sequencing requirements nearly 1000-fold.

To design compressive measurements, Applicants first consider the canonical basis described by Principle Component Analysis (PCA) as an example of an embedding for RNA-Seq data. Suppose, for the sake of argument, that Applicants knew of a universal set of 100 PCs, and that a linear combination of these could be used to describe the gene abundances in any system. By building molecular probes for each PC, Applicants could measure the response along each component in a given sample, and then take the linear combination of these 100 measurements to recover the abundance of every gene. Generally speaking, a basis that is universally appropriate for all systems (in a sense, this is an ultimate goal of biology) is not known. However, there is a surprising result which tells Applicants that making random measurements is universally appropriate for any basis that Applicants are likely to encounter [Compressive sampling. In Proc. Int. Congress of Math., Madrid, Spain, Aug. 2006.]. After making random measurements, and using methods of sparse coding [Efficient sparse coding algorithms. In NIPS, 2006.], Applicants can simultaneously infer the basis and its sparse contributions to the samples in question, and recover the desired signal.

Measurements may be made via hybridization with targeted gene probes, which are in certain embodiments labeled with a unique molecular identifier (UMI, such as barcoded) and sequenced to count hybridization events (see e.g. FIGS. 14A-14B and 25A-25C). In such case, each measurement uses a given collection of probes, and there may be multiple probes per gene. For one of m measurements, a random library may be constructed from a barcode pool, and a pool of gene-specific oligos. Each oligo in the barcode pool may contain one or more of a universal adapter, a cell/experiment ID, a molecular ID, a measurement ID (one of m total), and a linker region. Gene specific oligos may contain a complementary linker region, and a target sequence for the given gene. The final probe pool may be created by annealing and extension reactions.

The choice of probe sets may be a random design. Random probe sets have several advantages. Two random measurements are orthogonal (not correlated) with high probability, which means that each random measurement is effectively measuring something "new." This is difficult, if not impossible, to ensure when each measurement consists of a single gene, and, thus, random probes do a better job of maximizing the information content of a small number of measurements. Existence of a gene correlation structure is assumed without knowing what it is. The probe sets are substantially universally appropriate. By randomly scattering measurements throughout the transcriptome, it can be ensured that Applicants sample from the relevant structures with high probability. Applicants then employ computational methods of Sparse Coding to learn the basis, or gene expression structure which is appropriate for the sample at hand. Importantly, the learning is integrated into the same process for inferring the full gene expression profile, and does not require a separate set of measurements. The number of types of measurements can be approximated by k log (n), where k is an estimated value of sparsity.

At least two methods for randomizing the amount of probe for each gene in each library are considered. First, the molecular IDs are synthesized randomly. Each of these IDs are assigned to +1/−1, such that when counting hybridization events for a given measurement Applicants either increment or decrement the total depending on the molecular ID. Thus, Applicants could have the same number of probes for every gene in each measurement, but the sum across molecular IDs for a given gene is a binomial random variable. Alternatively, a Liquid Handling Robot may be used to mix the barcode and gene pools according to a randomly generated matrix. In either case, the probe library is sequenced after construction to determine its composition.

In the present system, measurements are read out via sequencing, after hybrid selection and amplification. The number of types of measurements is contemplated to be between approximately 100 and 30,000 different types of measurements. The number of types of measurements can be based on an estimate of system sparsity. The number of types of measurements per sample can be, for example, 100. To the extent that there is any knowledge of assumptions about certain measurements or between genes, the number and type of measurements may be adjusted. For each measurement barcode within a cell, Applicants can have gene specific probes for each of ~29k genes. However, the number of probes for a given gene will vary across each of the 100 measurements, according to random design. Once types of measurements are established, and the number or transcripts to be measured are determined, a Design Matrix having a number of rows corresponding to the number of types of measurements (measurement vectors) and the number of column corresponding to the number of transcripts can be generated. The Design Matrix is populated by "measurement values," which are random numbers of measurements such that for each type of measurement each transcript can be counted up to a relative number of times that is random and independent of other elements/entries in the Design Matrix. In other words, the relative number of times up to which a certain measurement type can count each respective transcript is random and independent of the relative number of times up to which that certain measurement type can count other transcripts in the sample and the relative number of times up to which a certain transcript can be counted for a certain type of measurement is random and independent of the relative number of times up to which that certain transcript can be counted for other types of measurement. While the measurements may be random and independent, such is not required. Knowledge of some relationships between measurements may allow manipulation of the measurement values to improve calculations. For example, steps according to the present application may be iterated multiple times to refine results by incorporating knowledge gained through a first round of measurements. Similarly, knowledge of relationships between genes, measurements and transcripts may be used to inform and select some measurement values for the Design Matrix, although this is not required. For example, the Design Matrix can be adjusted according to a known basis.

A probe library corresponding to the Design Matrix may be generated. For example, a probe library comprises 100 or more molecules assembled according to a set of random measurement values forming at least one measurement vector, where each molecule comprises a tag for the at least one measurement vector operably linked to a probe for one type of transcript of a plurality of types of transcripts. The probe library includes a collection of molecules assembled according to the measurement values, where each molecule has a tag, e.g., a barcode, for one of the measurement types operably linked to a probe for one of the types of transcripts. The tag may uniquely correspond to a measurement type/vector. Probes contemplated according to the present invention may be single-stranded DNA, transcript, protein, DNA, non-naturally occurring nucleic acid, peptide, or the like. That is, each amount of probe can thus be adjusted based on the random measurement values in the Design Matrix such that the amount of a specific probe is known relative to the amounts of the other probes based on the Design Matrix.

While the present example describes cells as the sample for measurement, the sample may include cells, blood, hair, nails, mucus, tissue, feces, urine, body secretion or the like.

For one application, measurements may be made in single cells, and probe sets may be held as oligos on beads. For example, in one aspect each oligo may hold at least one of a sequencing adapter, a cellular barcode, a measurement barcode, a molecular barcode, and a primary gene-specific probe. cDNA or RNA (such as mRNA) targets may be captured on the primary probes, and then secondary probes, which target sequences immediately adjacent to the primary probes, may be introduced. Ligation of the primary and secondary probes produces a full-length fragment that can be amplified via universal sequences on the 5' end of the bead-attached oligo, and 3' end of the free-floating secondary probe. After amplification, Applicants sequence the barcode-containing regions to count the number of molecular events for each cell/measurement barcode combination. Contacting the probe library to the pool of samples thus results in a number of measurement results for each cell of the pool of cells. An advantage of capturing RNA directly, instead of cDNA, is that the RT step can be omitted, such that overall bias or measurement error may be reduced.

The sample types are not limited to cells and may be any of numerous types of biomolecules. A biomolecule is any molecule that is present in living organisms, such as large macromolecules such as proteins, polysaccharides, lipids, and nucleic acids, as well as small molecules such as primary metabolites, secondary metabolites, and natural products. In an advantage embodiment, the biomolecule is a nucleic acid, such as but not limited to, deoxyribonucleic acid (DNA), ribonucleic acid (RNA), peptide nucleic acid (PNA) or other non-naturally occurring nucleic acid. In another advantageous embodiment, the biomolecule is a protein, such as but not limited to, peptides, antibodies, immunogenic molecules or enzymes.

An Observed Measurement Matrix may thus be constructed using the measurement results for each cell/sample to populate the elements/entries of the Observed Measurement Matrix. Construction of the Observed Measurement Matrix can include tag quantification, and tag quantification can include sequencing. For example, a relative count is conducted of the tags such that the relative number of times a certain tag is counted per cell is entered into an appropriate element of the Observed Measurement Matrix M. A sparse coding solving process may then be applied to the Observed Measurement Matrix M to learn system matrix S as indicative of relative abundance of the transcripts in each of the samples.

An example of a sparse coding process can be exemplified by $$\underset{m \times c}{M} = \underset{m \times n}{DM} \bullet \underset{n \times c}{S}$$

where m is the number of measurement vectors, c is the number of cell vectors, and n is the number of gene vectors. S is a System Matrix, which can be determined once M and DM are populated (M with actual measurements/counts and DM with random measurement values). S is thus indicative of the relative gene abundances.

Moreover, once S is known, a Basis Matrix B, can be determined based on knowledge of X, a matrix populated by known contributions of genes n and cells c to the sample.

$$\underset{n \times c}{S} = \underset{n \times n}{B} \bullet \underset{n \times c}{X}$$

Knowledge of the Basis can then be used to generate new measurement values of the Design Matrix to refine calculation of a new System Matrix S'.

In one embodiment of the present invention, the sparse coding solving process comprises the use of noisy compositional observations. In order to simulate m noisy compositional observations of each of n samples, the following matrix product may be used:

$$M=DM(S+\text{noise})$$

In one particular embodiment, the System Matrix S may represent the original gene expression profiles (g genes x n samples) and the Design Matrix DM has each of its m rows representing one of the random linear combinations of the n genes, with m«n. When noise is taken into consideration, the Observed Measurement Matrix M gives the m noisy linear combinations for each sample (m rows x c samples), according to the weights given in a row of the Design Matrix DM.

In some variants taking noise into consideration, the noise process for each gene in each sample is identically and independently distributed (i.i.d.), for example as a Gaussian. In some embodiments, the magnitude of the noisy components may be set by a signal-to-noise ratio, for example a signal-to-noise ratio of 2.

Due to sparsity of the system, the different interactions between genes may be treated as modules, wherein a module may be seen as a biological process in which each gene may or may not take part in a coordinated manner under a subset of conditions.

Figure 16:
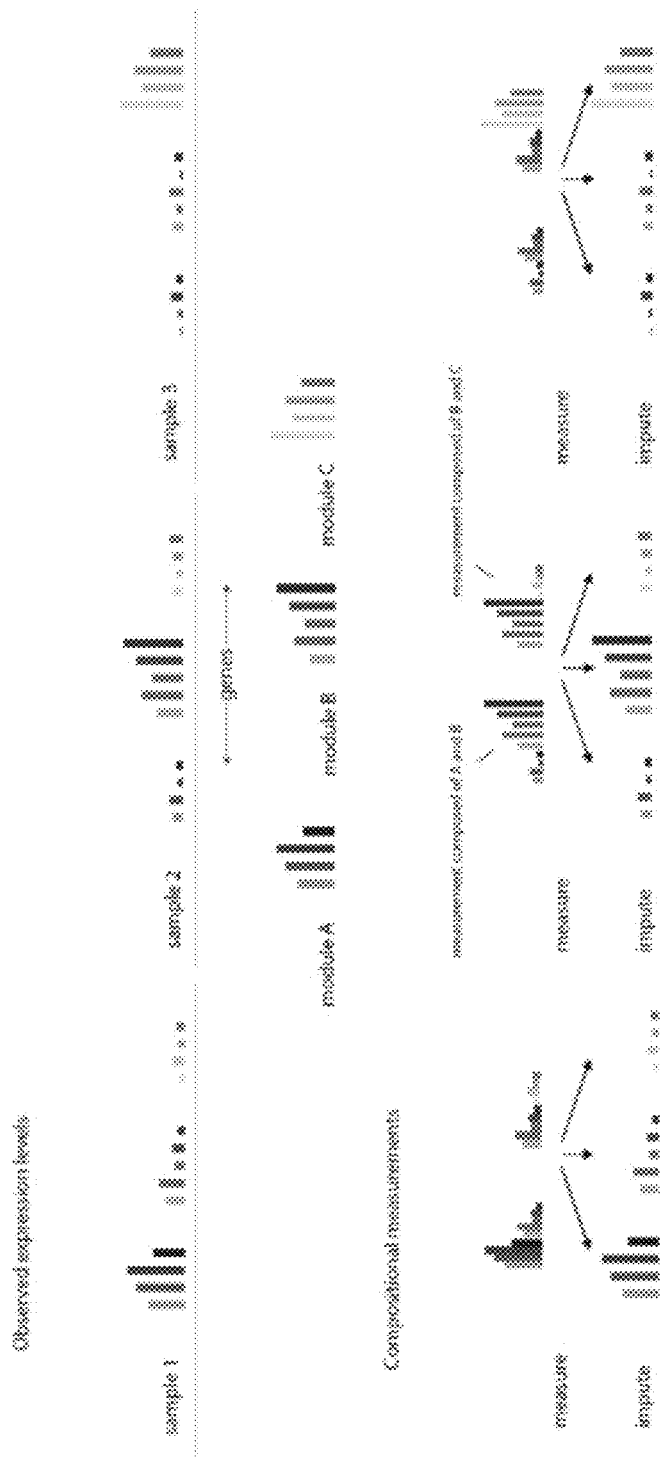
FIG. 16 illustrates how sparsity makes it possible to treat gene expressions as modules and to decrease the number of measurements needed to infer all expressions.

FIG. 16 illustrates how the sparsity of the system makes it possible to treat the different interactions between genes as modules. In this theoretical example, gene expression can be decomposed into the activity of three modules. If all three modules could be active, then a minimum of three measurements (corresponding to each module) would be required to infer gene abundance levels. However, because of sparsity, if each sample has only one active module, i.e. it is 1-sparse, then only two measurements per sample are needed:

a first measurement composed of modules A and B; and
a second measurement composed of modules B and C.

If module A is active, then only the first measurement will exhibit a high level of activity (left). If module B is active, then both the first and second measurements will exhibit a high level of activity (middle). Finally, if module C is active, then only the second measurement will exhibit a high level of activity (right).

In one embodiment, the matrix factorization step comprises at least one, preferably all, of the following:
setting the number of modules active in any sample at a relatively small number;
setting the number of genes in any module at relatively small number and the number of modules in which each gene participates to a relatively small number;
taking the assumption according to which different modules represent distinct pathways or programs and do not overlap too much with one another as a condition of the sparse coding solving process; and/or
setting the total number of modules at a not too large number.

In one sub-embodiment, the total number of genes being n, the number of active modules in any sample is set to be lower than 500, lower than 400, lower than 300, lower than 200, lower than 100, lower than 90, lower than 80, lower than 70, lower than 60, lower than 50, lower than 40, lower than 30, lower than 20, or lower than 10. In one sub-embodiment, the total number of genes being n, the number of active modules in any sample is set to be greater than 1, greater than 2, greater than 5, or greater than 10. In certain embodiments, the total number of genes being n, the number of active modules is between 1 and 500, or any possible sub-range within the stated range of 1 to 500, for example between 1 and 400, between 1 and 33, between 1 and 200, between 2 and 100, between 2 and 90, between 2 and 80, between 5 and 70, between 5 and 60, between 5 and 50, between 10 and 40, between 10 and 30, for example about 20.

In one sub-embodiment, the total number of genes being n, the number of genes in any module is set to be lower than 25,000, lower than 20,000, lower than 15,000, lower than 10,000, lower than 9,000, lower than 8,000, lower than 7,000, lower than 6,000, lower than 5,000, lower than 4,000, lower than 3,000, lower than 2,000, lower than 1,000, lower than 900, lower than 800, lower than 700, lower than 600, lower than 500, lower than 400, lower than 300, lower than 200, or lower than 100. In one sub-embodiment, the total number of genes being n, the number of genes in any module is set to be greater than 5, greater than 10, greater than 20, greater than 50, greater than 100, greater than 200, greater than 500, or greater than 1000. In certain embodiments, the total number of genes being n, the number of genes in any module is between 5 and 1000, 10 and 5,000, 20 and 5,000, 50 and 5,000, 100 and 5,000, 200 and 5,000, 500 and 5,000, 1,000 and 5,000, 1,000 and 10,000, 1,000 and 15,000, 1,000 and 20,000, 1,000 and 25,000, 5,000 and 10,000, 5,000 and 15,000, 5,000 and 20,000, 5,000 and 25,000, 10,000 and 15,000, 10,000 and 20,000, 10,000 and 25,000, 15,000 and 20,000, 15,000 and 25,000, 20,000 and 25,000. In certain embodiments, the total number of genes being n, the number of genes in any module is between 1,000 and 2,000.

In some embodiments, the total number of genes being n, each gene is present in at least one module.

In one embodiment, the total number of modules is between one tenth the number of samples to be analyzed and five times the number of samples to be analyzed. For examples, if the total number of samples is 1,000, the number of modules may be at least 100 and at most 5,000.

The System Matrix S of observed expression levels may be expressed as the product of the X matrix, which can also be considered as a dictionary of expression modules wherein each column is a vector of length n (one entry per gene) and is one element of the dictionary, and a Basis matrix B of module activity levels wherein each column describes a linear combination of columns of X. In other words, X reflects the possible modules and B the level of expression of each module. Abundance levels may be approximated as a linear combination of gene modules. In a very general sense, any decomposition of multiple expression profiles in the following form fits with this interpretation. Posed in this way, this becomes a problem of matrix factorization: S=BX. In order to solve the equation, the sparse coding solving process thus may comprise a matrix factorization step. In one embodiment, the matrix factorization step comprises non-negative matrix factorization (NMF). In Nonnegative Matrix Factorization (NMF), all the entries of the module dictionary matrix and the basis matrix are nonnegative. NMF has the advantage that, like gene expression values themselves, the coefficients in the module dictionary and the module activity levels are not allowed to take on negative values. In some embodiments, a specific version of this algorithm (Sparse NMF) also constrains the number of active modules in each sample to be small: additional sparsity constraints are enforced on the activity levels, such that there are relatively few nonzero entries in B. Nonnegativity is sensible for expression analysis, since negative expression levels don't exist, but one might expect that some modules are actively repressed, and that this might be best represented with negative activity coefficients. Moreover, typically in Sparse NMF, there are no sparsity constraints on the module dictionary, and so one might find that most genes participate in most modules.

Alternatively, the matrix factorization step comprises Sparse Module Activity Factorization (SMAF). As used herein, SMAF is defined as having two important properties. First, both the module dictionary and the module activity levels are required to be sparse. Second, the entries of the dictionary matrix X is required to be nonnegative (because these values are meant to be interpreted as "membership" in a module), but the entry of the basis matrix B may be either positive or negative (because modules can either be activated or repressed).

SMAF makes it possible to improve ability to recover representations that are not just reduced in dimensions and sparse but also yield modules with relatively few genes and distinct biological features.

Like some algorithms for sparse NMF, SMAF optimization may proceed through alternating updates to X and B:

(1) initialize a random $X$, $B$;

(2) update $X$: $\min_X \|X\|_1$ such that $\|S - BX\|_2^2 < \lambda_X$, $u_{i,j} \geq 0$, and $\|x_i\|_2 = 1$ for all $i$ and $j$;

(3) update $B$: $\min_B \|B\|_1$ such that $\|S - BX\|_2^2 < \lambda_B$.

Steps 2 and 3 may be iterate until convergence, or until a desired sparsity eve is reached. In some embodiments, the algorithm is initialized with the output of another matrix factorization method, such as sparse NMF. In some embodiments, a random initialization is used. In practice, the best results were found with a random initialization, although this may take more iterations to converge. The parameters $\lambda_X$ and $\lambda_B$ can be used to set a desired level of accuracy.

With each matrix factorization algorithm, preferably sparse NMF or SMAF as discussed above, the number of dictionary elements may be specified. For sparse NMF, a truncated decomposition is preferably used, keeping the vectors corresponding to the largest singular values. In some embodiments, a minimally sized dictionary with at least a 99% fit to the original data is used:

$$\text{fit} = 1 - \frac{\|S - BX\|_2^2}{\|S\|_2^2}$$

With SMAF, the desired fit according to constraints may be set in steps 2 and 3, as discussed above. In some embodiments, the SMAF dictionary size is set to be 4 times the size of the sparse NMF dictionary, without being larger than min(500,1.5·c).

In an aspect of the present invention, the sparse coding solving process comprises compressed sensing (CS) using training data to learn the system matrix S. For example, using training sets, $S_{training}$, a module dictionary weight may be calculated via matrix factorization:

$S_{training} \approx BX$

In some embodiments, the training set consist of a fraction, preferably at least 1% and at most 10%, of the samples in a given dataset, for example the training set may consist of about 5% of the samples in a given dataset. Preferably, the matrix factorization is performed using sparse NMF or SMAF, as described above.

In a following step, simulated compositional measurements may be performed on the testing samples (for example 95%):

$M = DM(S_{testing} + \text{noise})$ where the Design Matrix DM defines the random composition of n genes in each of m measurements (as before, with m«g). For a given module dictionary ($X_{NMF}$, or $X_{SMAF}$), the module activities, $\hat{B}\tilde{B}$, that best fits the observations is preferably sought, so that:

$S \approx DM\hat{B}X$

The optimization may be performed while enforcing sparsity in $\hat{B}$, for example so that there are no more than 5 active modules per sample, for example so that there are no more than 10 active modules per sample, for example so that there are no more than 15 active modules per sample. The module activity coefficients in each testing sample may then be used to compute predicted gene expression values, $\hat{S}=\hat{B}X$.

In some embodiments, the problem is written as:

$$M \approx DB$$

and the spark of D is bound. For example, by choosing random Gaussian entries in the measurement matrix, the spark condition is satisfied with high probability.

In another aspect of the present invention, the sparse coding solving process comprises Blind Compressed Sensing (BCS) to learn the system matrix S. This presents the advantage, which has been unheard of till this day, that the BCS approach is not limited by training data, particularly by the nature of the training data and model used for imputation. Indeed, training data necessarily introduces biases in learning a model. In some embodiments, the dictionary is learned from low-dimensional composite measurements. In some embodiments, the module activity levels and the gene abundances may be inferred, without ever observing high dimensional gene expression patterns.

Blind Compressed Sensing may be reduced to the problem of learning a good (i.e. sparsely activated) dictionary. Once the dictionary is fixed, the previously discussed matrix factorization methods may be used to recover the activity coefficients. To get the dictionary, a dictionary learning algorithm with high dimensional input is preferably used. Initially, the high dimensional input may consist of (possibly very poor) approximations to gene abundances, based on low dimensional observations and the composition of each measurement. A small number of composite measurements may generate a good first approximation of a sparsely activated module dictionary.

In an aspect of the present invention, the sparse coding solving process comprises sparse module activity factorization (SMAF) for the matrix factorization step and blind compressed sensing (BCS) to learn the system matrix S. SMAF may be used to find the initial sample clusters and modules for BCS. Given the SMAF approximation, the dictionary may be updated using standard algorithms, then the module activity levels may be updated, and then all three steps may be iterated. For example, noisy composite measurements may be simulated across a randomly selected subset of genes.

Variable Gaussian measurements are preferably used; for each sample m compositional observations may be generated using different measurement matrices, DMi. The BCS-SMAF algorithm preferably proceeds as follows:

1. Get initial estimates of each sample as: $\hat{s}_i = DM_i^T (DM_i^T DM_i)^{-1} m_i$.
2. Based on current estimates, calculate SMAF($\hat{S}$): $\hat{S} \approx \hat{B}\hat{X}$.
3. Update estimate of the dictionary with a standard dictionary learning (DL) algorithm, using $\tilde{X}$ $\tilde{X}$ for initialization: $\hat{X}=DL(\hat{S}, \tilde{X})$.
4. Estimate module activities using Orthogonal Matching Pursuit: for each column $\hat{b}_i = OMP(m_i, DM_i\hat{X}, k)$.
5. Iterate steps 2-4.
6. Return the estimated signals: $\hat{S}=\hat{B}\hat{X}$.

The present invention enables both to design new ways to compress biological systems and to better understand the organization and regulation of gene expression and biological processes. First, it is possible to recover the high-dimensional representation of n abundance levels (e.g. 20,000, which correspond roughly to the number of genes in a mammalian genome) from a collection of many fewer measurements. Indeed form the fewer measurements, it is possible to recover the active module(s) and thus the full expression profile for any sample/cell.

Further, the knowledge of a dictionary of universal programs (modules), and the activation of these programs across cell types could teach us a great deal about biological systems and gene regulation. E.g. it makes it possible to identify the key functional modules active in a biological sample and help infer the regulatory mechanisms that control them.

FIGS. 17 to 25 illustrate the particular advantages of using NMF and SMAF as sparse coding methods over others.

Figure 17:
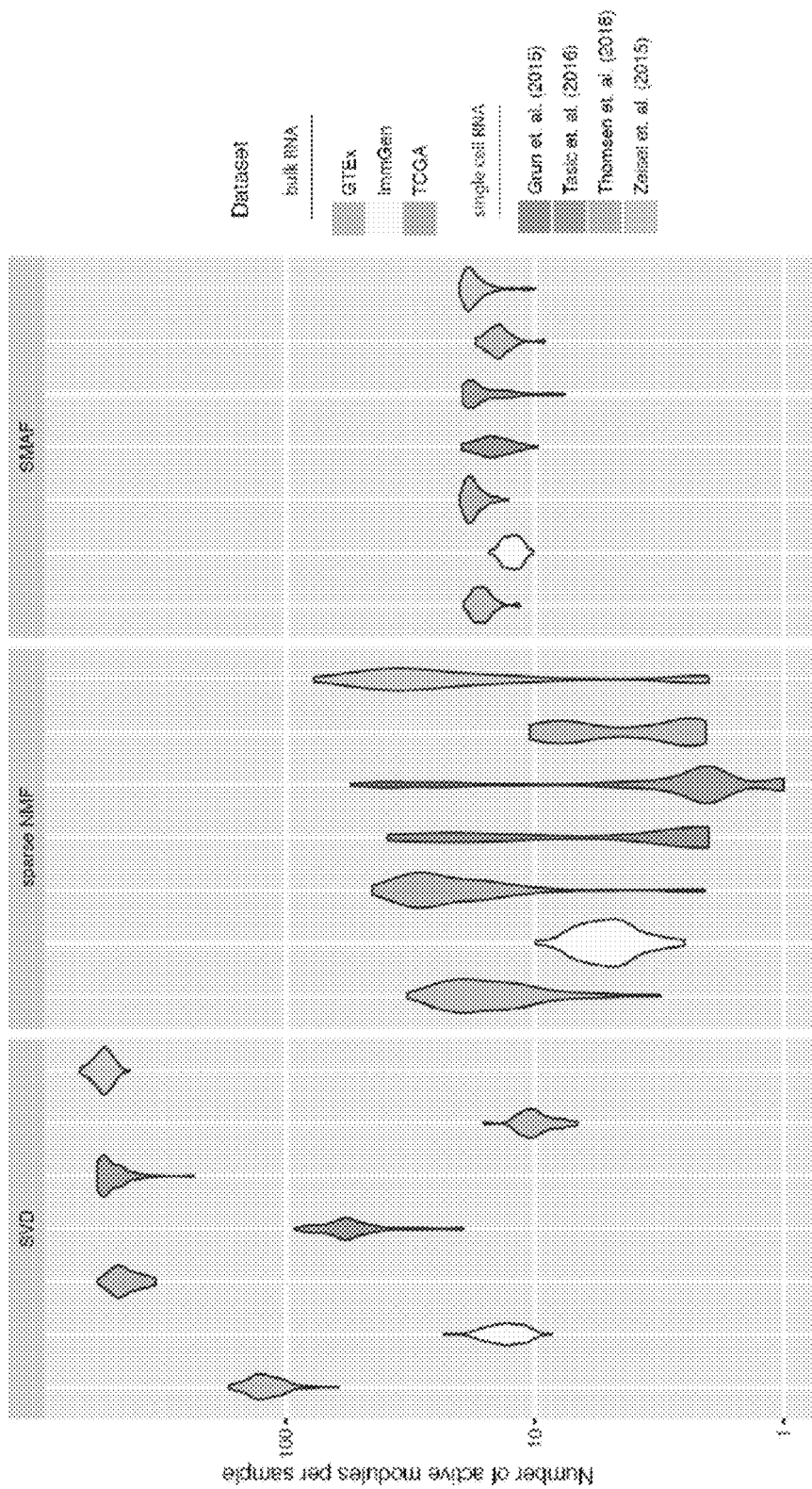
FIG. 17 illustrates a comparison between three sparse coding methods (SVD, sparse NMF, and SMAF) with respect to effective number of modules.
Figure 18:
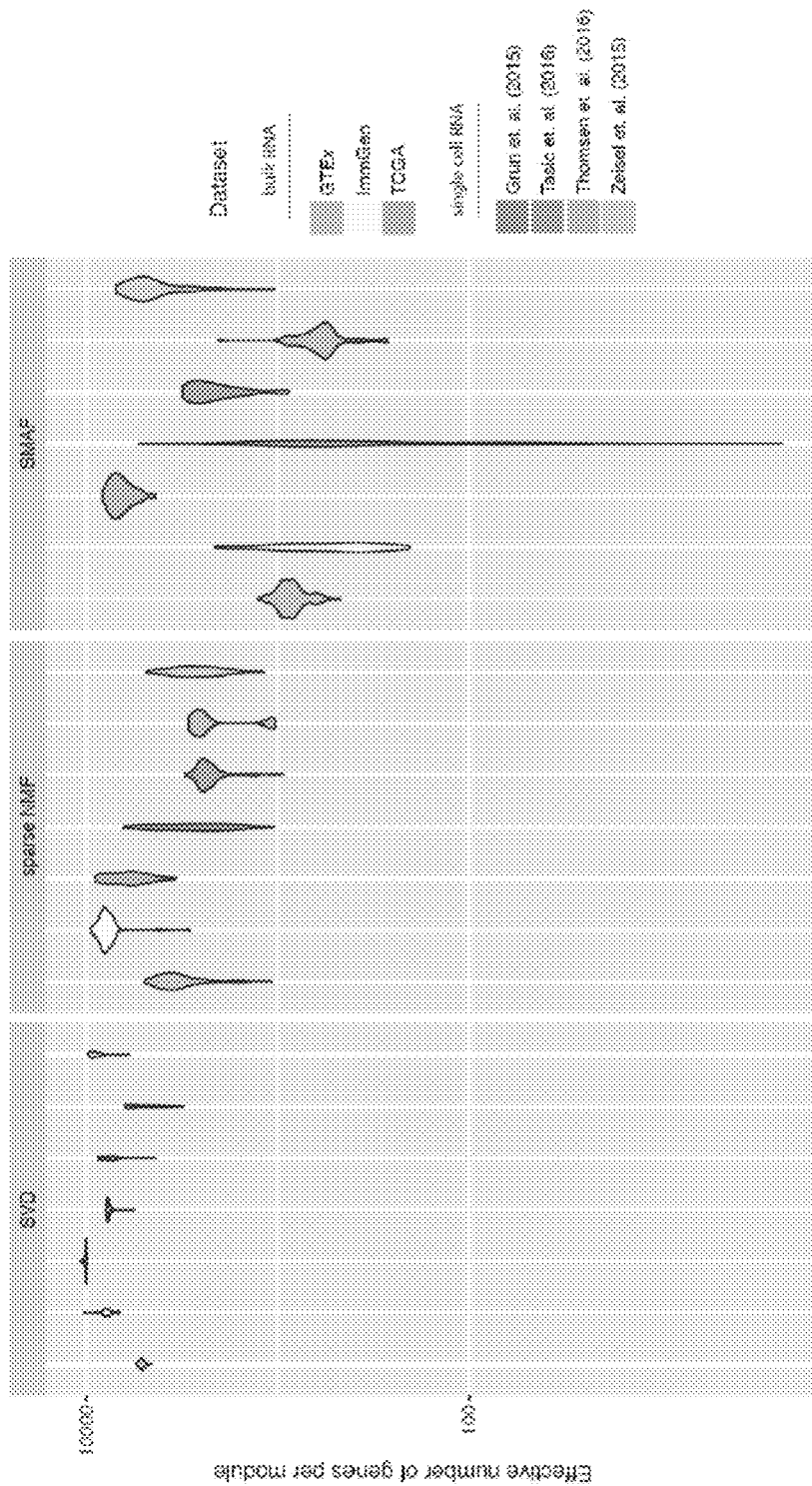
FIG. 18 illustrates a comparison between three sparse coding methods (SVD, sparse NMF, and SMAF) with respect to distribution of module sizes.
Figure 19B:
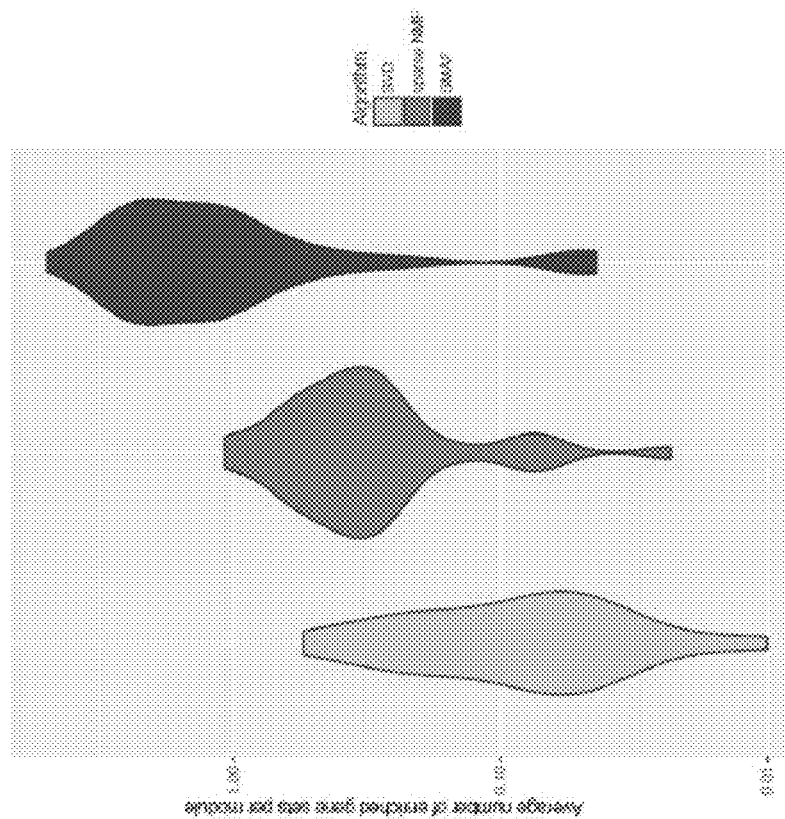
FIG. 19B illustrates a comparison between three sparse coding methods (SVD, sparse NMF, and SMAF) with respect to average number of unique gene sets per module.
Figure 19A:
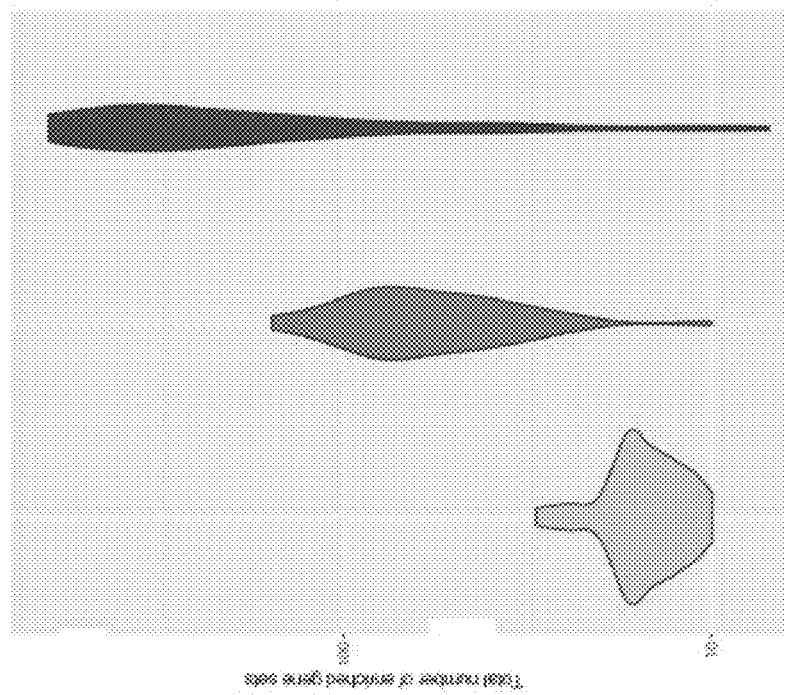
FIG. 19A illustrates a comparison between three sparse coding methods (SVD, sparse NMF, and SMAF) with respect to total number of gene sets enriched in at least one module.

In FIGS. 17 to 19, three different matrix factorization algorithms (SVD, sparse NMF, and SMAF) were used to analyze seven (7) datasets. three bulk RNA datasets: GTE, ImmGen and TCGA; four single cell RNA datasets: Grun et al. Nature. 525:251-5 (2015), Tasic et al. Nat. Neurosci. advance on, 1-37 (2016), Thomsen et al. Nat. Methods. 13:87-93(2016) and Zeisel et al. Science 347:1138-42 (2015).

SVD, Singular Value Decomposition, is one of the best known algorithms for matrix factorization in gene expression analysis: Alter et al. Proc. Natl. Acad. Sci. U.S.A. 97:10101-106 (2000).

Each algorithm produces a module dictionary and module activity levels in each sample that are consistent with observed expression levels. In FIG. 17, the effective number of active modules for each sample in a dataset is shown in a violin plat. In FIG. 18, the distribution of module sizes is shown, in terms of the effective number of genes participating in each module. Gene set enrichment analysis was performed on the set of genes in each module, preferably by comparing genes in a module to genes in known databases. For each dataset (shown as a point in FIGS. 19A-19B), the total number of gene sets enriched in at least one module (left), and the average number of unique gene sets per module (right) could be counted. The results show that SVD did not generally recover a sparse representation: samples were frequently represented by a linear combination of hundreds of modules, whereas sparse NMF could generally fit the data well (88.6% fit on average across all datasets) while also producing sparse solutions, with 5.1 active modules per sample on average, as could SMAF (93% fit on average; while producing sparse dictionaries and sparse activity levels; average of 1.45 uniquely enriched gene set per module, without truncation; total number of gene sets enriched in at least one module much greater with an average of 372 enriched gene sets per dataset, versus 63 with sparse NMF). Using only the top genes for each module (genes found to be most active in the module) improved the enrichments, but only moderately so (from 1.45 unique sets per module to 1.62). In this way, the modules produced by SMAF were found to be readily interpretable. It was found that the SMAF algorithm constrained by assumptions of sparsity and modularity can explain most of the information in gene expression and that the discovered dictionary of gene modules appears to be biologically meaningful.

Figure 20:
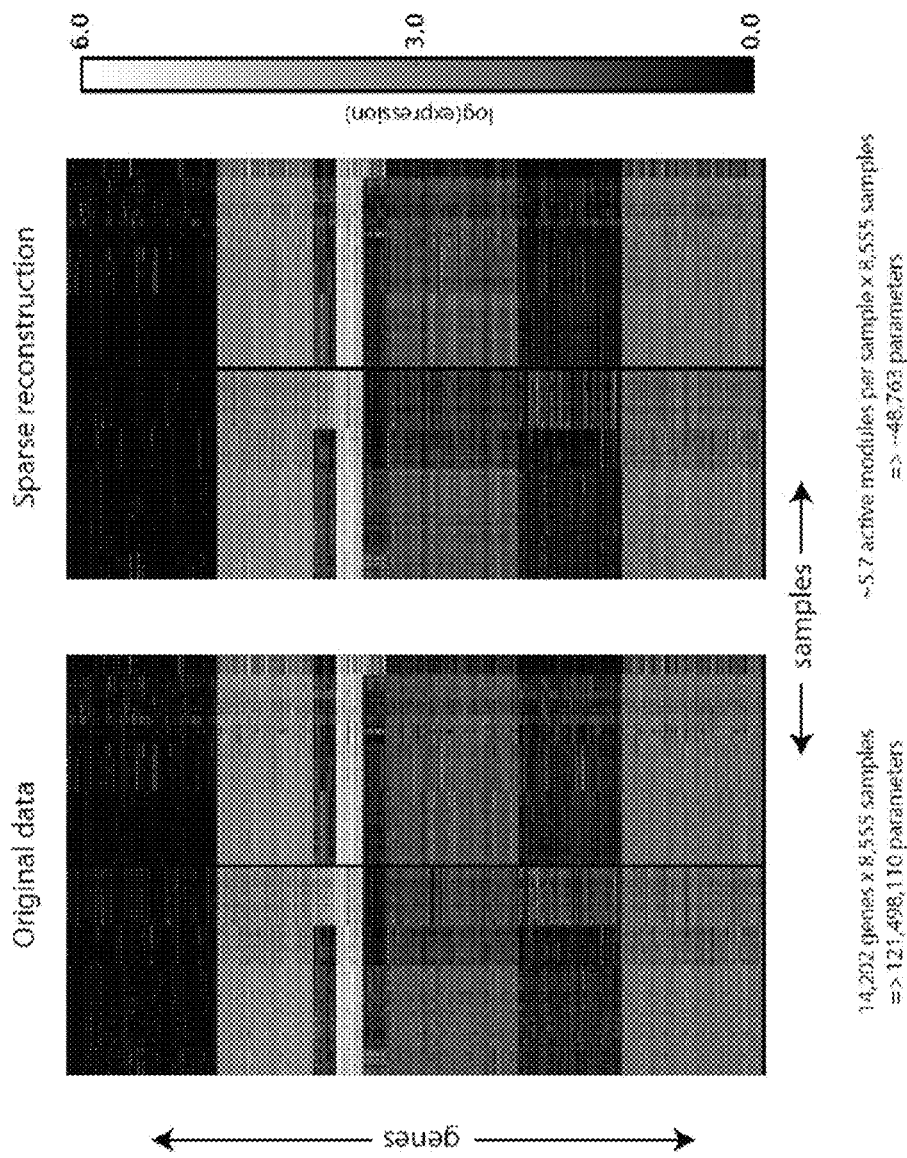
FIG. 20 illustrates a comparison between gene expression profiles of dataset GTEx with the expression levels reconstructed using SMAF for the same dataset.

FIG. 20 gives a comparison of visualization of GTEx gene expression profiles (left) with expression levels reconstructed from SMAF (right) for the same dataset.

Figure 21:
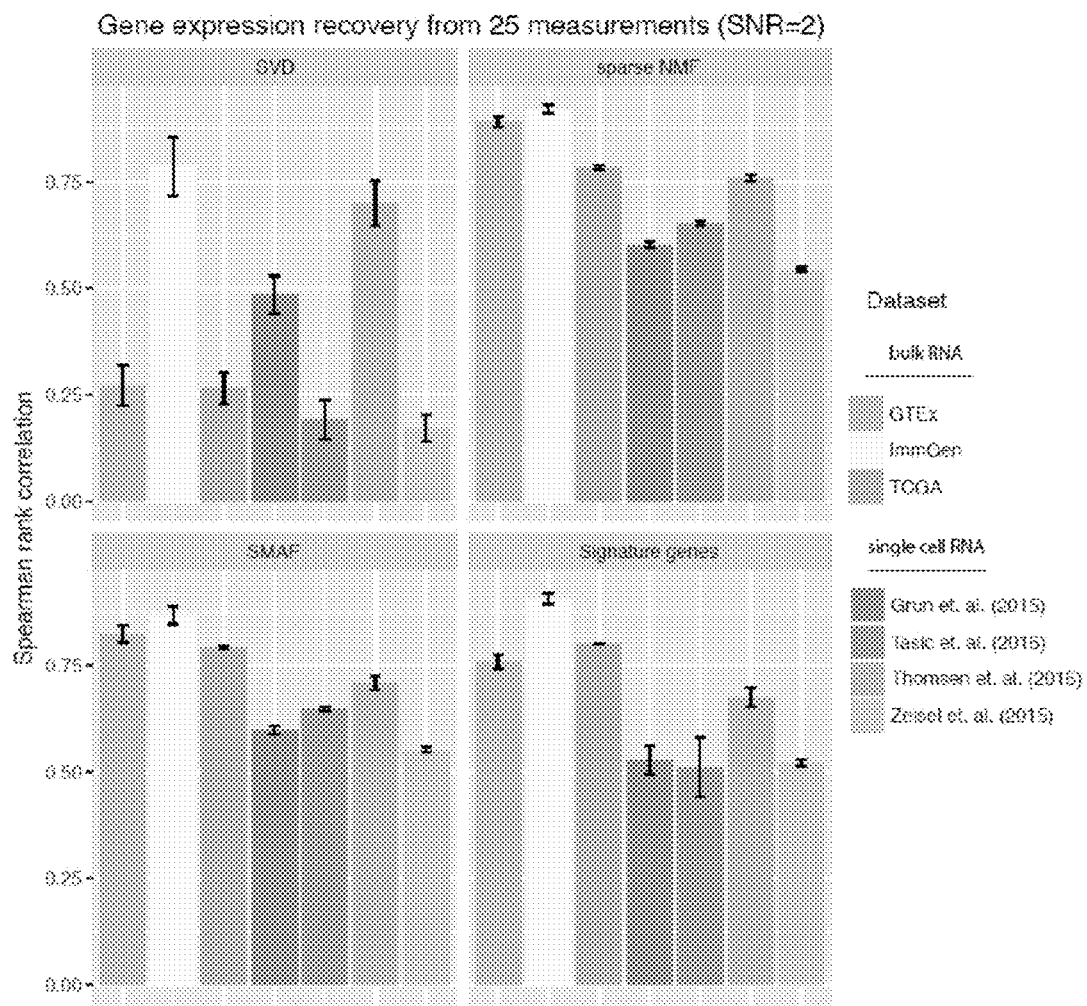
FIG. 21 is a bar graph illustrating a comparison between three sparse coding methods (SVD, sparse NMF, and SMAF) and signature gene analysis.
Figure 22:
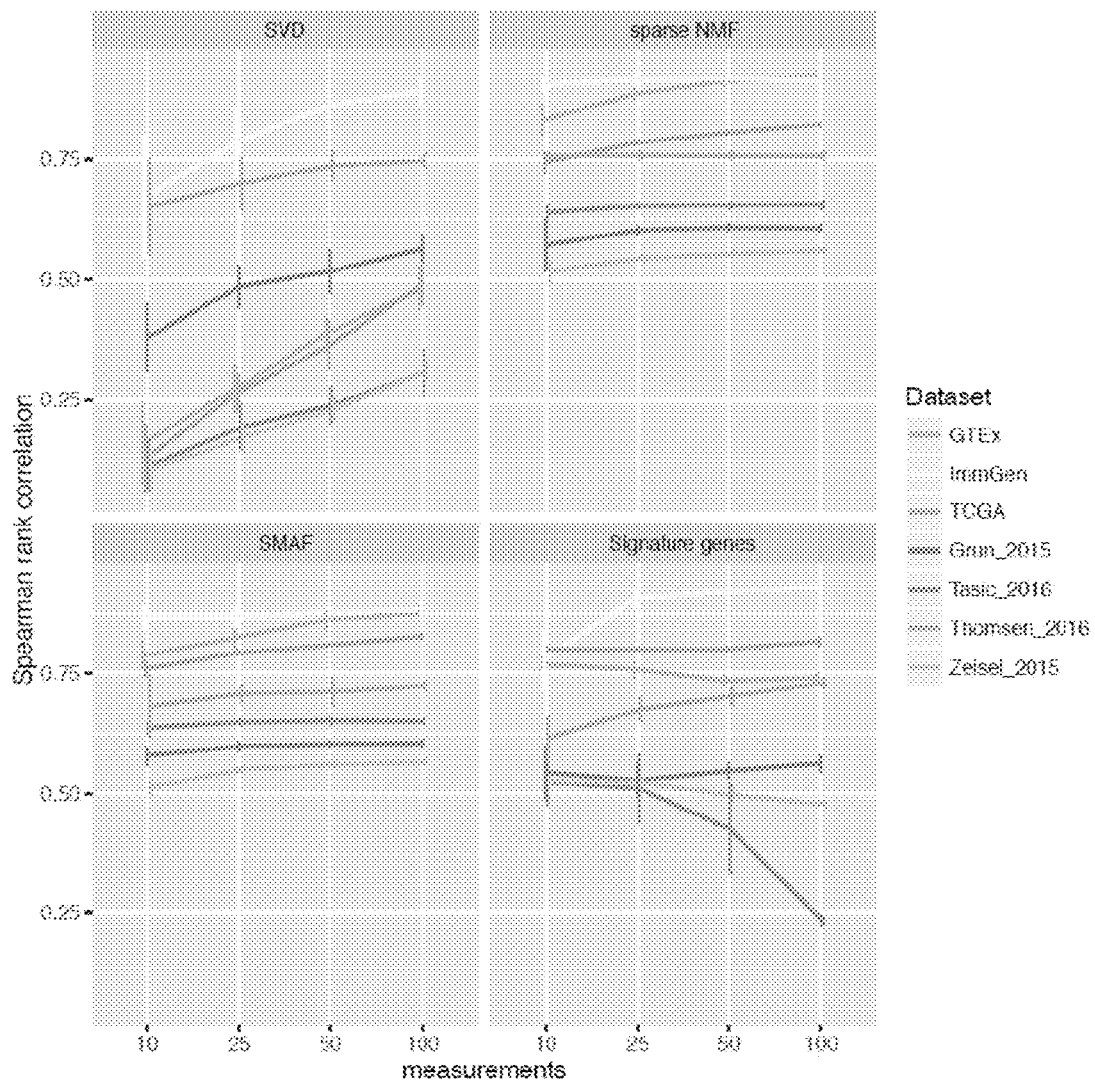
FIG. 22 is a line graph illustrating a comparison between three sparse coding methods (SVD, sparse NMF, and SMAF) and signature gene analysis.

FIGS. 21 and 22 illustrate gene expression profiles that are recovered using three sparse coding method and signature gene analysis when the module dictionary is known. For each dataset (same as for FIGS. 17 to 19) each tested method was used to predict 5,000 gene abundance levels across a set of training samples based on a small number of measurements, preferably between 10 and 200. Sparse coding methods (SVD, sparse NMF, and SMAF) were used to define module dictionary and measurements consisted of noisy, random compositional measurements. For signature gene analysis, measurements consisted of a number of individual genes. In FIG. 21, the bar heights depict the Spearman correlation of predicted and original expression levels for each algorithm using 25 measurements, averaged across 50 random trials. In FIG. 22, each algorithm was run multiple times with different numbers of measurements. Error bars indicate on standard deviation in Spearman correlation, across 50 random trials. Successful recovery of gene expression from compressed measurements rests on samples actually having a sparse representation in the given dictionary, i.e. there being not too many active modules in each sample. The comparison shows that this approach indeed worked well for dictionaries based on sparse NMF or SMAF, but not SVD. Spearman rank correlations were consistently found to be lower for SVD than sparse NMF and SMAF. The results for 10 measurements have surprised the Applicant in that correlations for sparse NMF and SMAF were relatively very good: 83% for NMF and 79% for SMAF.

Figure 23:
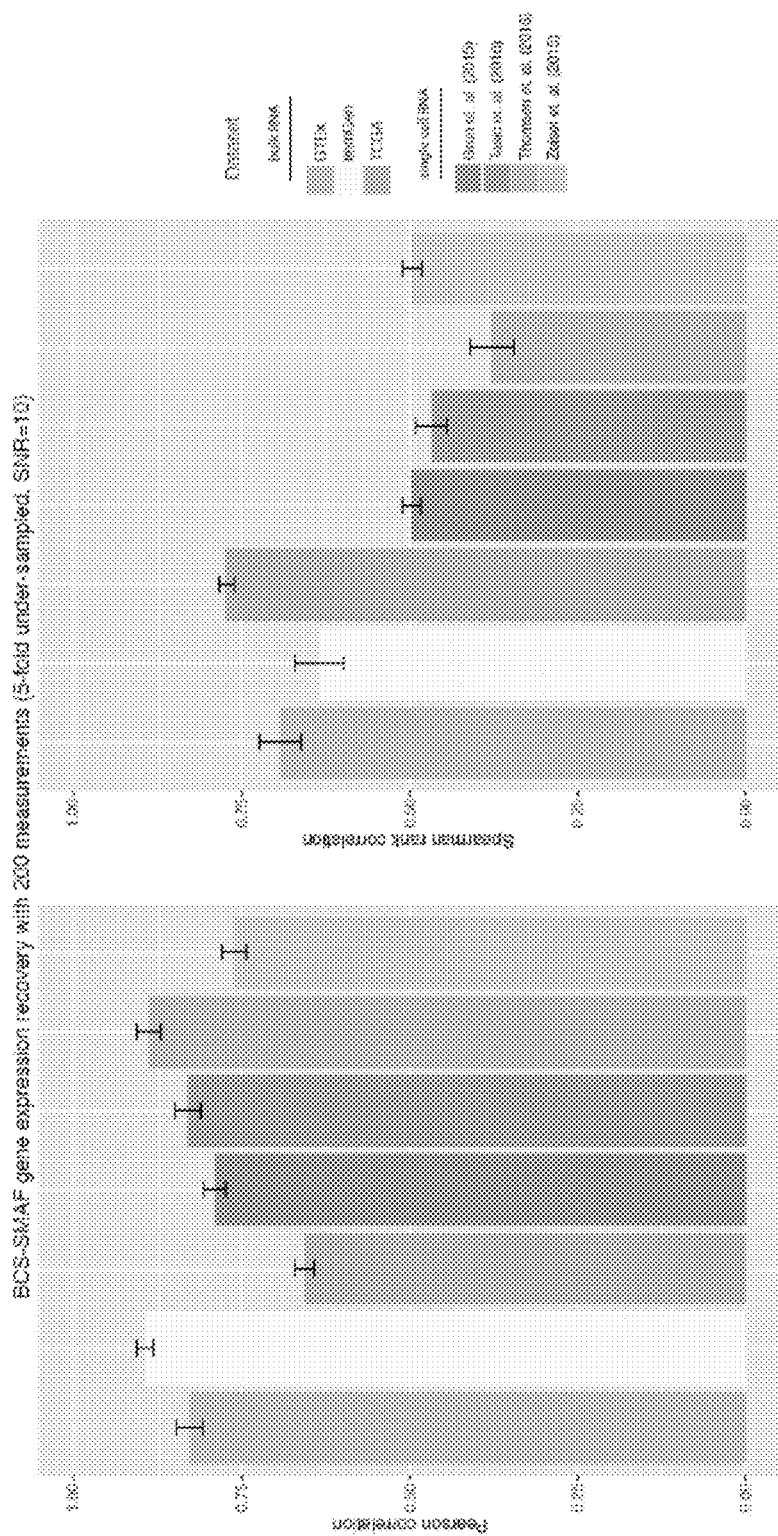
FIG. 23 illustrates results obtained from blind compressed sensing with SMAF: Pearson and Spearman rank correlations for each tested dataset based on 100 measurements.
Figure 24:
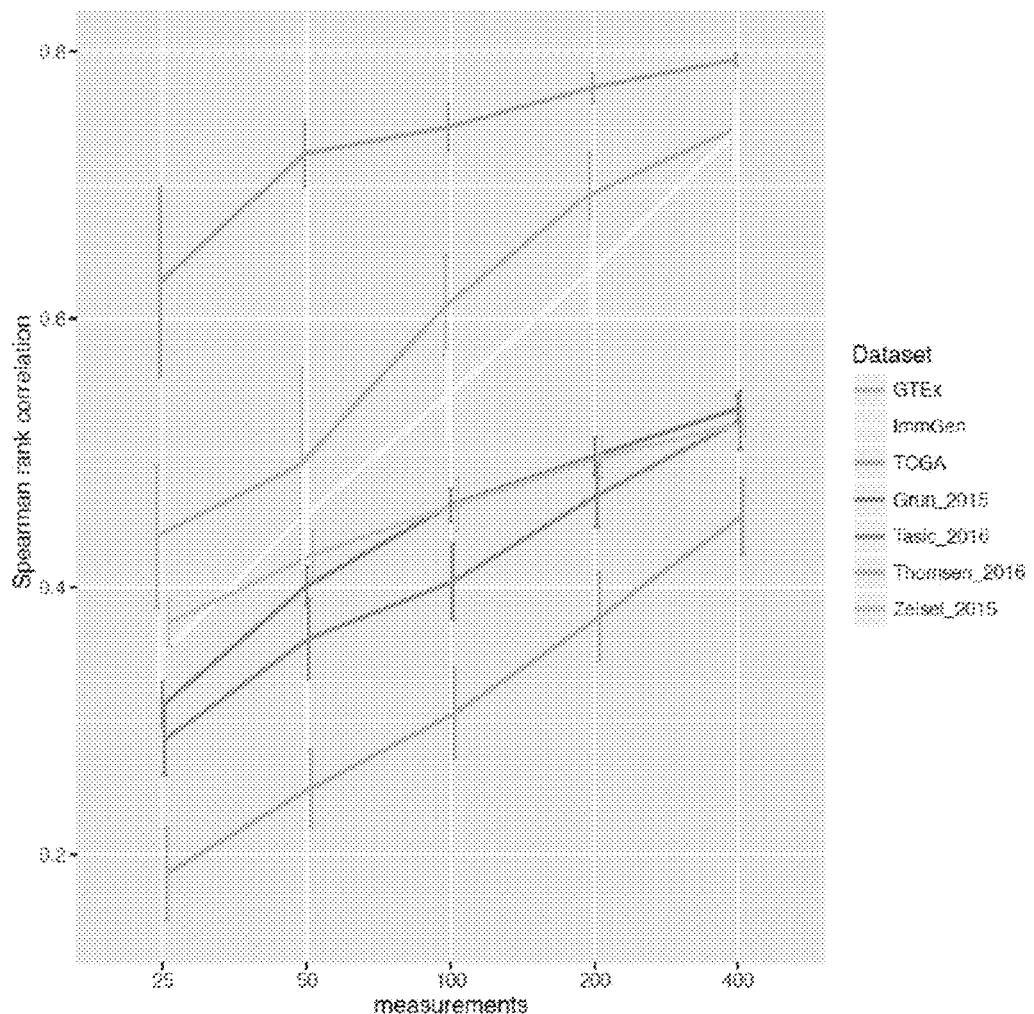
FIG. 24 illustrates Spearman rank correlation for each tested dataset and for different numbers of measurements in each dataset.
Figure 25A:
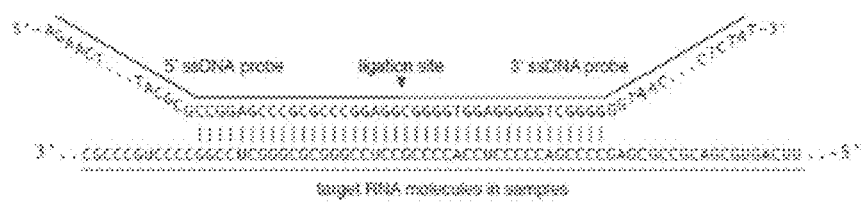
FIG. 25A shows design of the paired sensing probe-sets (PSPs). Two single-stranded DNA oligonucleotides (ssDNA oligos) were designed to bear sequences capable of hybridizing to adjacent regions on an RNA molecule (cyan and magenta) and measurement-specific barcode (PSP index, dark blue).
Figure 25B:
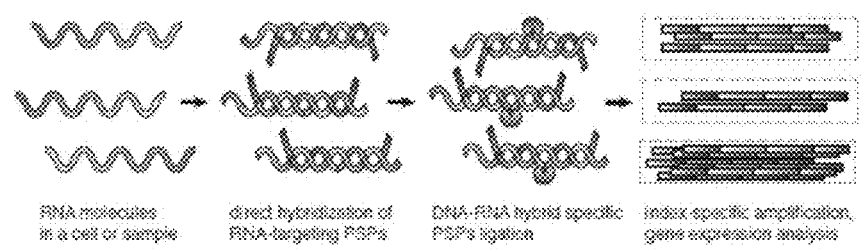
FIG. 25B displays that PSPs for each gene within a given measurement group share a common PSP index. All probes from all pools are annealed to the sample RNA, and a ligation reaction is carried out by an RNA-DNA hybrid specific ligase. For each pool, the net abundance of ligated probes is then measured by qPCR amplification with measurement-specific primers.
Figure 25C:
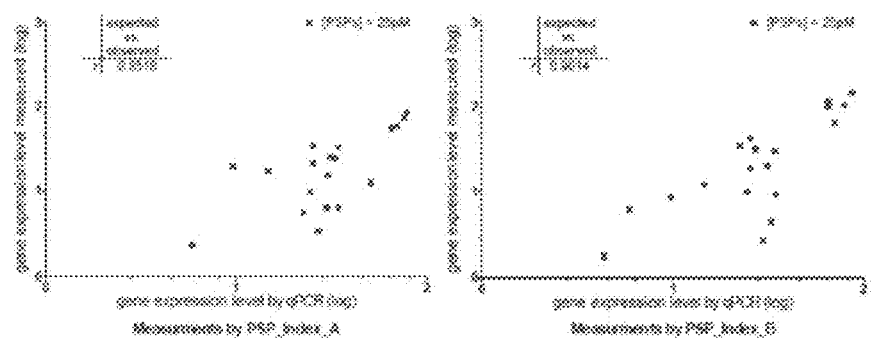
FIG. 25C demonstrates that two PSP pools with different common primer (PSP_Index_A and PSP_Index_B) were used for measurement of gene expression level in K562 total RNA to demonstrate accuracy and robustness of the workflow.

The same was done with blind compressed sensing using SMAF. The results are illustrated in FIGS. 23 and 24. Expression levels were approximated from compositional measurements without access to any training samples. For each dataset in FIG. 23, 500 gene abundance levels were approximated across all training samples based on 100 random compositional measurements. Bar heights (error bars) depict the average (standard deviation) Pearson (left) and Spearman (right) correlation across 50 random trials. In FIG. 24, performance was measured for different numbers of measurements in each datasets. Although the performance was expectedly worse than results with a known dictionary, the recovered abundance levels were still significantly correlated with the original values. For example, the expression profiles recovered by blind compressed sensing using SMAF from 200 random composite measurements of GTEx data (5-fold under-sampled) had 82% Pearson and 69% Spearman correlations with the unobserved values, averaged across simulation trials. Increasing the number of measurements had a dramatic effect on recovery performance (FIG. 24).

Testing for linearity of hybrid selection is contemplated, along with dynamic range, by, for example, splitting bulk cDNA prepared from a population of K562 cells. In one split, qRT-PCR is performed for a collection of 25 genes that range from the highest abundance, to being absent. In a second split, hybrid selection is tested on a collection of 24 random probe libraries (3 experimental IDs, each with 8 measurement indices). The goal is to optimize the hybridization conditions for maximal dynamic range, while ensuring that the readout from sequencing after hybridization is linear with regards to qPCR controls, and the amount of probe for a given gene in a given library. The size of the probe library is then successively increased to 100 genes, then 1000, and finally to the set of all genes. The measurements are more robust with larger panels of genes, since Applicants' readout is effectively the sum of hybridization events across all probes for a given measurement index. In other words, since only barcodes are sequenced the barcodes and not the gene specific regions, the process is not sensitive to the stochastic capture of transcripts for any single gene, but rather to the average capture across all genes. Finally, this design is compatible with single cell technologies, and has indeed been designed with this application in mind. In particular, random probe libraries held on beads in place of barcoded poly-dT oligos are contemplated, but this is just one of many possible constructions.

In a first round of experiments, Applicants have constructed the random probe sets as follows. One pool of oligos is synthesized to contain a universal sequence, a cellular barcode, a measurement barcode, a molecular barcode, and a linker region. A second pool is synthesized to contain a complimentary linker region, and a gene-specific target. Oligos from the two pools can be annealed, and then extended in the 3' direction on the barcoded fragment with the Klenow fragment, or T4 DNA polymerase. These can be treated with lambda exonuclease, and purified by size selection for the full-length fragment. This can be done for each gene, and then the fragments can be mixed and pooled according to random design. Alternatively, fragments for each gene in each measurement can be pooled in equal amounts. In this case, Applicants achieve random measurements by assigning each molecular identifier (which was synthesized randomly) to a +1/−1. When integrating the counts for a given measurement, Applicants then increment or decrement the count according to this assignment. Since the molecular barcodes and assignments are made randomly, the sum of +1/−1 assignments for a given gene behave as a random variable across the different measurements. Secondary gene probes can be synthesized independently.

It is anticipated that probe libraries may be constructed and provided and present methods applied to provide cost-effective gene-expression profiling. Accordingly a product comprising completed probe libraries, or a kit for making the libraries according to principles of the present invention are possible. For some applications it may make sense to focus on a subset of genes, in which case the kit would be particularly appropriate.

In addition, random probes and sparse coding could be applied as a service. That is, a customer may provide a sample or sample pools to an entity for constructing a probe library according to customer objectives and sample, applying the steps of the methods according to principles of the present invention and providing as its result a report of the relative gene-abundances or gene-expression profile or the like. This could be particularly useful for applications that require the analysis of tens to hundreds of thousands of transcriptional profiles, since Applicants estimate that methods according to principles of the present invention reduce sequencing requirements by 100-1000 fold. For example, when screening for combinatorial effects of small molecules, or when testing for the presence of very rare cell types (such as cancer stem cells), a large number of profiles need to be generated.

Rapidly advancing experimental methods are opening new ground for the exploration of higher-order genetic interactions. These methods include the CRISPR-Cas system for knockouts, which enables greater degrees of combinatorial perturbations, as well as high-throughput readout techniques such as single-cell RNA-Seq. The ability to sequence the transcriptomes of tens of thousands of cells using droplet microfluidics has recently been demonstrated [Macosko et. al., 2015]. By constructing a polyadenylated RNA barcode that is associated with a CRISPR sgRNA, Applicants were able to couple the experimental scale of microfluidic technologies with perturbation experiments in mammalian cells. An example CRISPR screening method that may be improved by used of the methods disclosed herein is described at Datlinger et al. bioRiv (2016) dx.doi.org/10.1101.083774.

However, even with these advances, Applicants are limited to full combinatorial samplings of second- or third-order interactions for a small number of genes. For example, for a collection of 30 genes, performing all third-order knockouts is at the boundary of experimental feasibility (30 choose 3=4060 experiments), while a dense sampling of fourth-order terms for the same size collection (30 choose 4=27405), or third-order terms for a larger collection (100 choose 3=161700) is intractable. Therefore, Applicants are motivated to identify schemes that leverage Applicants' ability to perform combinatorial perturbations, while also dramatically under-sampling the full combinatorial space.

Compressive Sensing the Transcriptome

1st Trial Run—Analysis

Probe Library Creation

The new protocols generated a much higher percentage of fragments of the correct size (eg 70-99% stitched) as compared with the original L1000 protocol (19-42% stitched). Having larger cDNA input also resulted in a greater percentage of stitched fragments.

UMI Counting

Correlations of individual gene counts with expectation based on RPKM from ENCODE were generally positive, but not stunning. Results with gene counts from qPCR were largely unchanged. For the new ligation protocols, correlations were generally positive, except for row1 which generally has low (negative) values. For the L1000 ligation protocol correlations were more consistently positive, except for condition 21, which shows negative correlations for many rows/conditions.

Applicants also considered UMIs aggregated across genes, with randomly chosen rows. This mimics the intended setting. In this case correlations were generally much higher (range 47-79%). The best condition by this measure was 26_27 (new protocol with low ligation, low L/R ratio with undiluted cDNA).

The normalization strategy used in initial trials is based on sequenced barcode counts from direct ligation of probes, without cDNA targets. Quantifying barcode counts in this way gives an overall estimate of the abundance of each member of the library. In future experiments, we will compare the results of this normalization strategy to a normalization based on ligation to a pool of genomic DNA.

X18 samples (3 FBC vs 6 RBC)

<P5 barcoding>

Original L1000: P5-30

New protocol (high ligation 5 ul mix input for R1, see notes below): P5-25

New protocol (low ligation 1 ul mix input for R1, see notes below): P5-26

<P7 barcoding>

1. High L/R ratio probe mix+5 μL cDNA input (~50 ng/μL): P7-14
2. High L/R ratio probe mix+5 μL (⅛ diluted) cDNA input (~6 ng/μL): P7-21
3. Low L/R ratio probe mix+5 μL cDNA input (~50 ng/μL): P7-27
4. Low L/R ratio probe mix+5 μL (⅛ diluted) cDNA input (~6 ng/μL): P7-28
5. High L/R ratio probe mix direct ligation with T7:P7-15
6. Low L/R ratio probe mix direct ligation with T7:P7-20

Read Counts

| F | R | Total Fragments | Stitched | % Stitched |
|---|---|---|---|---|
| 26 | 27 | 799365 | 795574 | 99.5% |
| 25 | 27 | 890612 | 881037 | 98.9% |
| 26 | 20 | 839036 | 825118 | 98.3% |
| 26 | 14 | 401287 | 383828 | 95.6% |
| 26 | 28 | 628901 | 589907 | 93.8% |
| 26 | 21 | 237079 | 217109 | 91.6% |
| 25 | 14 | 124932 | 109626 | 87.7% |
| 26 | 15 | 1067299 | 906534 | 84.9% |
| 25 | 15 | 1033888 | 838764 | 81.1% |
| 25 | 28 | 726668 | 570421 | 78.5% |
| 25 | 20 | 849166 | 628951 | 74.1% |
| 25 | 21 | 65325 | 46374 | 71.0% |
| 30 | 20 | 437882 | 186679 | 42.6% |
| 30 | 14 | 774238 | 257647 | 33.3% |
| 30 | 15 | 938377 | 268906 | 28.7% |
| 30 | 21 | 745495 | 144001 | 19.3% |
| 30 | 28 | 1066525 | 189338 | 17.8% |
| 30 | 27 | 966163 | 149402 | 15.5% |

Correlation with RPKM

For each read Applicants parse barcodes into structures such as:

cell1 AGGTCGTA row1 ACTB ACTB

Stitched reads that do not fit this format are discarded. For direct ligation (no cDNA), Applicants allow the left and right gene barcodes to differ, but for all others Applicants require that the gene barcodes are identical.

Once parsed, Applicants count the number of UMIs for every gene in each condition and row (8 rows per condition). After normalizing by the number of UMIs in the corresponding direct ligation condition, Applicants can compare the normalized UMI count with actual RPKM for each gene.

Figure 3:
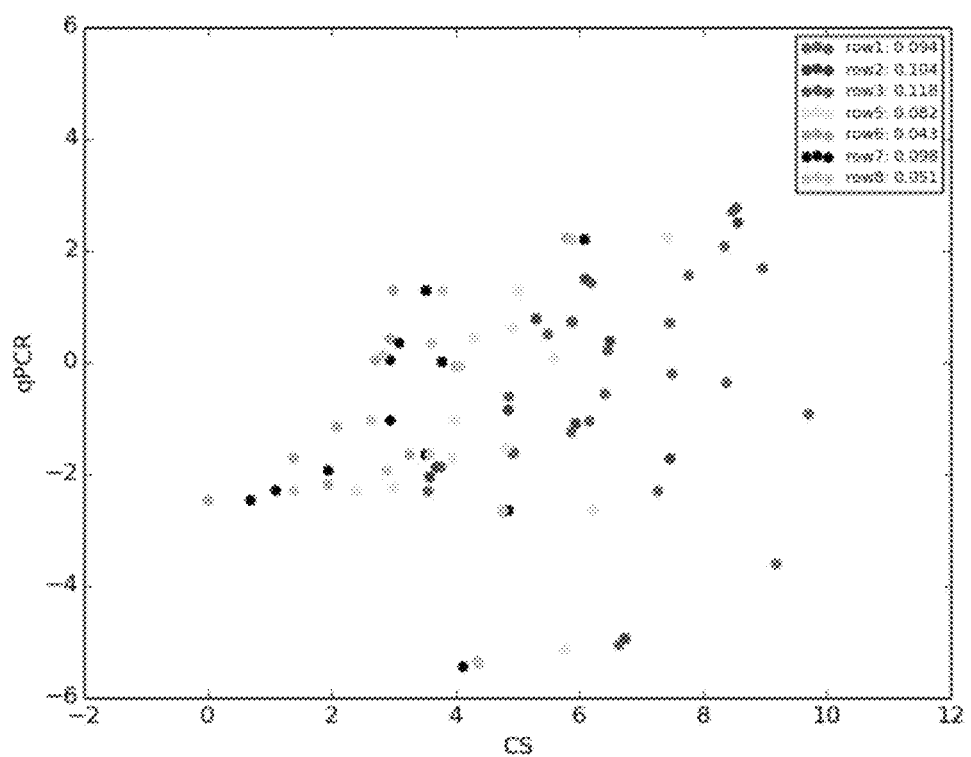
FIG. 3 is a plot of expected counts versus observed counts for a predetermined set of probes under a certain dilution criteria.

For a given experimental condition, probes were included at 8 dilution levels (rows 1-8). In row 1, probes for all targets were included at approximately the same concentration. In each successive dilution level (rows 2-8) the overall concentration of probes was serially diluted so that the probe concentration in row 8 was approximately 100-fold lower than the concentration in row 1. Thus, correlations of observed versus expected counts within each of the 8 dilution levels of a given experiment reflect the sensitivity of each assay across a 100-fold change in probe concentration. Correlations from these results are included at the end of this document. In FIG. 3 the results for one example condition (24_26) are depicted in a scatter plot.

Figure 4:
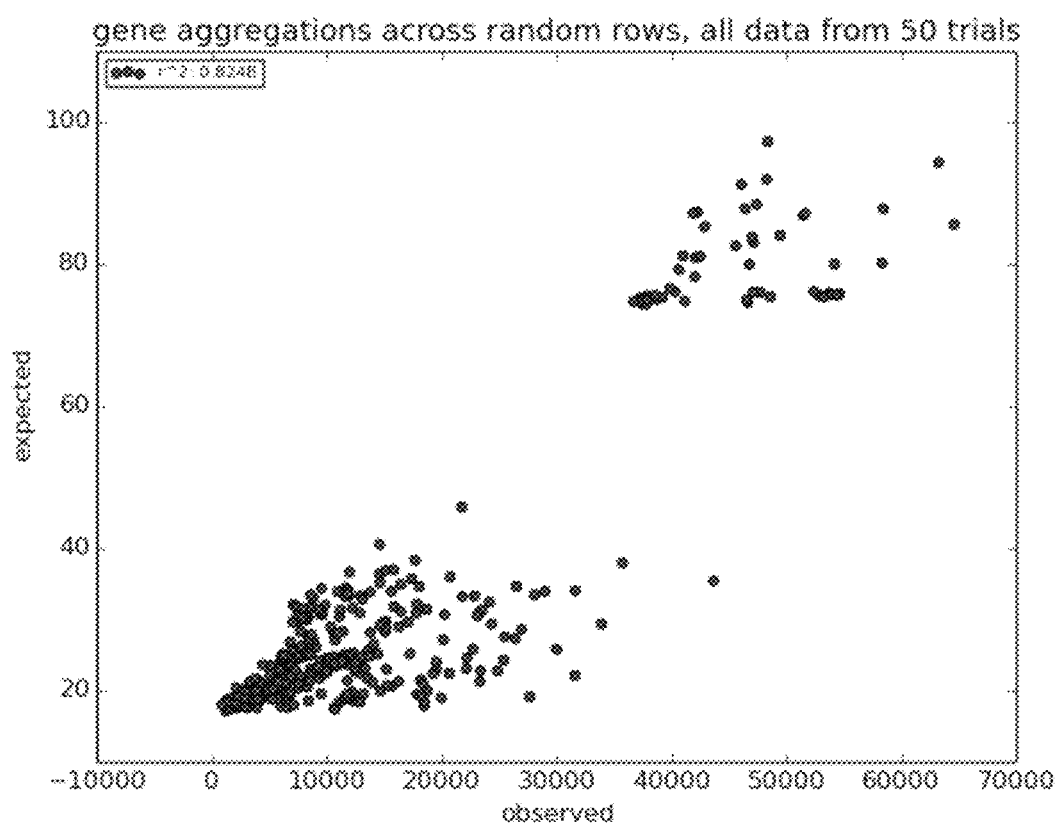
FIG. 4 is a plot of gene aggregations (observed versus expected) across random rows of a measurement vector for a 50 trial experiment.

Applicants can also ask how each condition would perform in the random setting where Applicants aggregate counts across all genes. To do this Applicants begin with a single gene, and choose a random row from the given condition. Applicants increment the "observed" count by the number of UMIs for that gene in that row, and increment the "expected" count by the product of the direct ligation UMI count for that gene/row with the RPKM of the gene. This is repeated for every gene such that Applicants have "observed" and "expected" sums across all genes with randomly chosen rows. This was repeated 8 times to generate a vector of random observations and expectations. Below Applicants report the correlation of these vectors for each condition, averaged across 50 random trials. In FIG. 4 the simulation results for one example condition (24_26) are depicted in a scatter plot.

| condition | correlation |
|---|---|
| 25_21 | 46.6% |
| 25_14 | 49.0% |
| 26_21 | 52.9% |
| 30_14 | 57.8% |

-continued

| condition | correlation |
|---|---|
| 30_27 | 63.4% |
| 30_21 | 65.0% |
| 30_28 | 68.9% |
| 25_27 | 69.7% |
| 26_14 | 70.2% |
| 25_28 | 74.1% |
| 26_28 | 76.6% |
| 26_27 | 79.3% |

Results for individual genes in each condition (condition IDs offset by 1):
norm.24_13.row1.txt:correlation: 0.101860
norm.24_13.row2.txt:correlation: 0.198498
norm.24_13.row3.txt:correlation: 0.125971
norm.24_13.row5.txt:correlation: 0.184587
norm.24_13.row6.txt:correlation: −0.065662
norm.24_13.row7.txt:correlation: 0.548366
norm.24_13.row8.txt:correlation: 0.188612
norm.24_20.row1.txt:correlation: 0.018865
norm.24_20.row2.txt:correlation: 0.011796
norm.24_20.row3.txt:correlation: −0.067194
norm.24_20.row5.txt:correlation: −0.220015
norm.24_20.row6.txt:correlation: −0.157439
norm.24_20.row7.txt:correlation: 0.364206
norm.24_20.row8.txt:correlation: 0.080670
norm.24_26.row1.txt:correlation: 0.372970
norm.24_26.row2.txt:correlation: 0.778385
norm.24_26.row3.txt:correlation: 0.794532
norm.24_26.row5.txt:correlation: 0.501830
norm.24_26.row6.txt:correlation: 0.340869
norm.24_26.row7.txt:correlation: 0.562235
norm.24_26.row8.txt:correlation: 0.576566
norm.24_27.row1.txt:correlation: 0.381881
norm.24_27.row2.txt:correlation: 0.771273
norm.24_27.row3.txt:correlation: 0.684149
norm.24_27.row5.txt:correlation: 0.445928
norm.24_27.row6.txt:correlation: 0.170683
norm.24_27.row7.txt:correlation: 0.543163
norm.24_27.row8.txt:correlation: 0.530076
norm.25_13.row1.txt:correlation: 0.309518
norm.25_13.row2.txt:correlation: 0.490934
norm.25_13.row3.txt:correlation: 0.349481
norm.25_13.row5.txt:correlation: 0.397947
norm.25_13.row6.txt:correlation: 0.272807
norm.25_13.row7.txt:correlation: −0.158994
norm.25_13.row8.txt:correlation: 0.256215
norm.25_20.row1.txt:correlation: 0.141412
norm.25_20.row2.txt:correlation: 0.275601
norm.25_20.row3.txt:correlation: −0.170215
norm.25_20.row5.txt:correlation: −0.115663
norm.25_20.row6.txt:correlation: −0.306711
norm.25_20.row7.txt:correlation: −0.590045
norm.25_20.row8.txt:correlation: −0.327281
norm.25_26.row1.txt:correlation: 0.513396
norm.25_26.row2.txt:correlation: 0.135664
norm.25_26.row3.txt:correlation: 0.493248
norm.25_26.row5.txt:correlation: 0.592195
norm.25_26.row6.txt:correlation: 0.649929
norm.25_26.row7.txt:correlation: 0.638488
norm.25_26.row8.txt:correlation: 0.592366
norm.25_27.row1.txt:correlation: 0.435686
norm.25_27.row2.txt:correlation: −0.043748
norm.25_27.row3.txt:correlation: 0.249897
norm.25_27.row5.txt:correlation: 0.615696
norm.25_27.row6.txt:correlation: 0.591814
norm.25_27.row7.txt:correlation: 0.550319
norm.25_27.row8.txt:correlation: 0.433558
norm.29_13.row1.txt:correlation: −0.351870
norm.29_13.row2.txt:correlation: 0.144392
norm.29_13.row3.txt:correlation: 0.057765
norm.29_13.row5.txt:correlation: 0.393736
norm.29_13.row6.txt:correlation: 0.031146
norm.29_13.row7.txt:correlation: 0.043738
norm.29_13.row8.txt:correlation: 0.382760
norm.29_20.row1.txt:correlation: −0.092086
norm.29_20.row2.txt:correlation: 0.040947
norm.29_20.row3.txt:correlation: 0.265565
norm.29_20.row5.txt:correlation: 0.589432
norm.29_20.row6.txt:correlation: 0.117522
norm.29_20.row7.txt:correlation: 0.386742
norm.29_20.row8.txt:correlation: 0.557595
norm.29_26.row1.txt:correlation: −0.218187
norm.29_26.row2.txt:correlation: 0.578199
norm.29_26.row3.txt:correlation: 0.549576
norm.29_26.row5.txt:correlation: 0.131541
norm.29_26.row6.txt:correlation: 0.271451
norm.29_26.row7.txt:correlation: 0.429337
norm.29_26.row8.txt:correlation: 0.189393
norm.29_27.row1.txt:correlation: −0.246045
norm.29_27.row2.txt:correlation: 0.449658
norm.29_27.row3.txt:correlation: 0.425474
norm.29_27.row5.txt:correlation: 0.376062
norm.29_27.row6.txt:correlation: −0.444794
norm.29_27.row7.txt:correlation: −0.125790
norm.29_27.row8.txt:correlation: 0.399004

Figure 5:
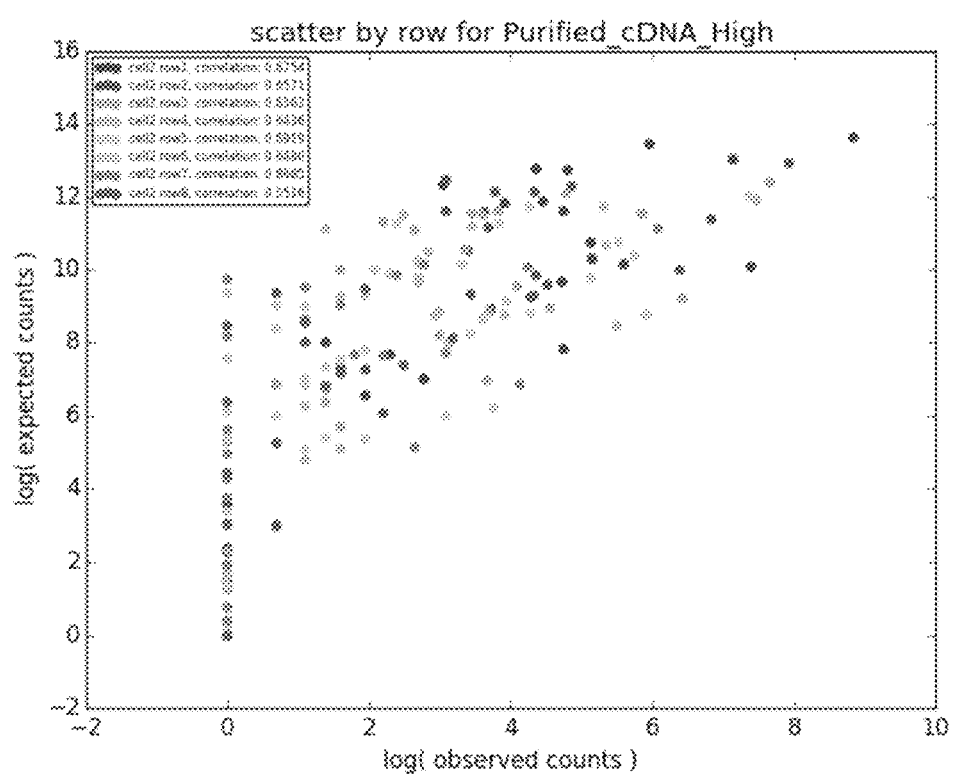
FIG. 5 is plot of expected counts versus observed counts for a predetermined set of probes under a certain dilution criteria for Purified cDNA High.

In a second round of optimizations, the probe library was expanded to target 24 genes that range from the most abundant, to non-abundant in the sample. As illustrated in the plots exemplified in FIGS. 5-8, correlation values for individual dilution levels (rows 1-8) were significantly higher than initial experiments. Correlation levels may be determined for a probe library and various dilution conditions of that probe library. For example, FIG. 5 is plot of expected counts versus observed counts for a predetermined set of probes under a range of dilution criteria for the protocol Purified cDNA High. In the experiment exemplified, 24 different genes from most abundant to not present were measured and correlation values determined within a dilution level, where a correlation of closer to 1 indicates a higher degree of correlation. In the first dilution level (row 1), probes for each of 24 genes were included at approximately equal abundance. In the second dilution level (row 2) the overall concentration of probes was reduced by a factor of 2. Each row down to row 8 was successively diluted, so that the concentration of probes in row 8 was approximately 100-fold lower than in row 1. Thus, the 8 correlation values in FIG. 5 represent the sensitivity of the assay across a 100-fold change in the concentration of gene probes.

Figure 6:
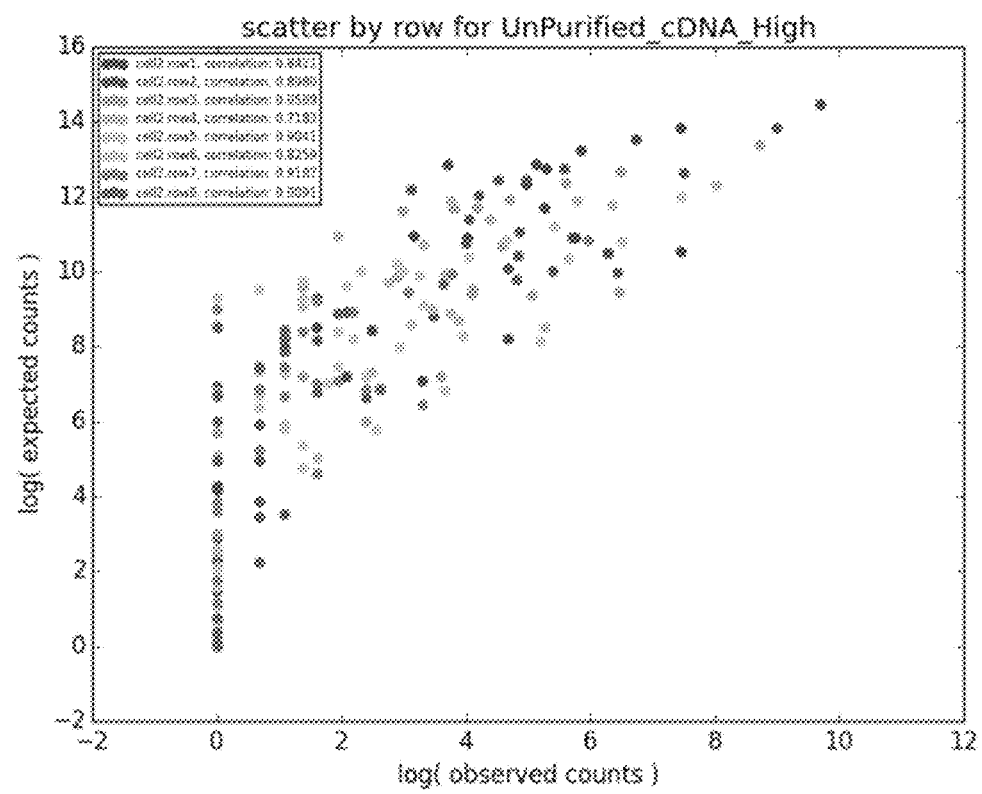
FIG. 6 is plot of expected counts versus observed counts for a predetermined set of probes under a certain dilution criteria for unPurified cDNA High.

Similarly, FIG. 6 is plot of expected counts versus observed counts for a predetermined set of probes under a range of dilution criteria for unPurified cDNA High.

Figure 7:
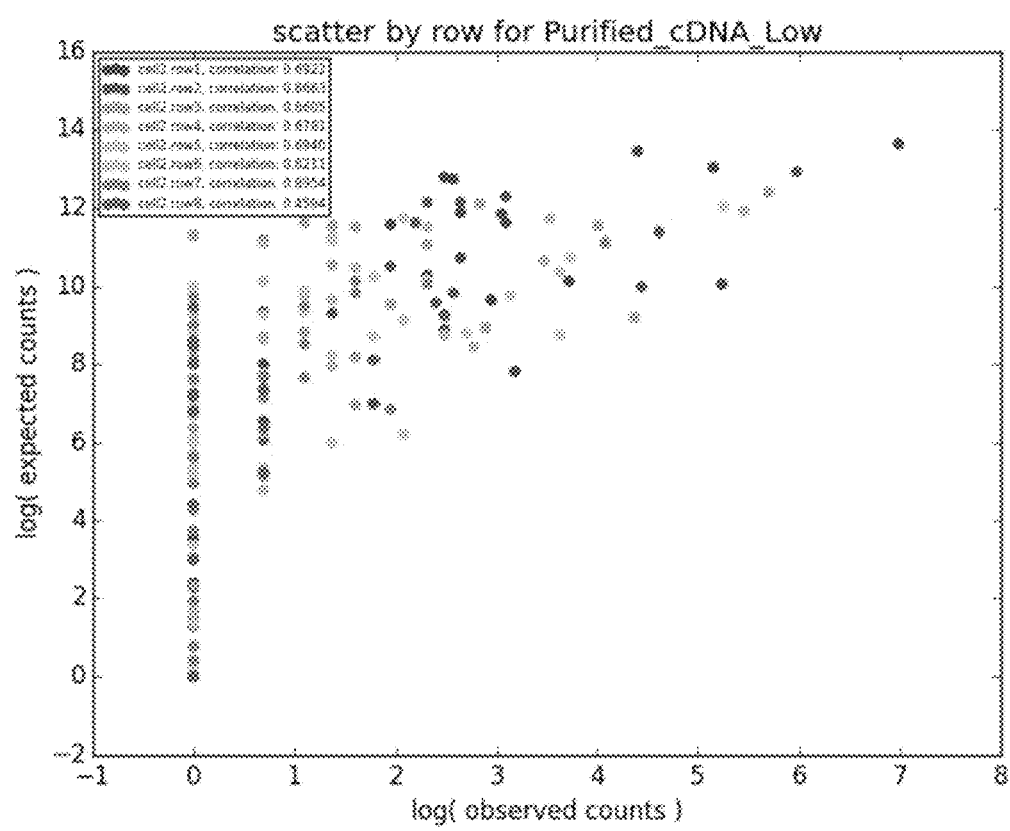
FIG. 7 is plot of expected counts versus observed counts for a predetermined set of probes under a certain dilution criteria for Purified cDNA Low.

FIG. 7 is plot of expected counts versus observed counts for a predetermined set of probes under a range of dilution criteria for Purified cDNA Low.

Figure 8:
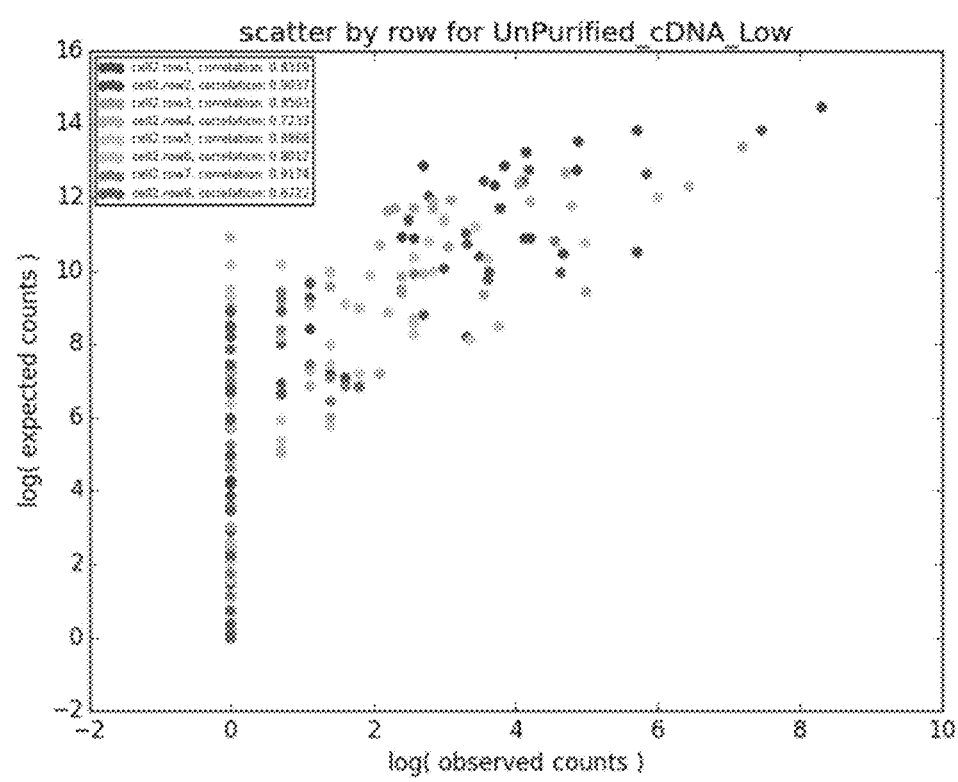
FIG. 8 is plot of expected counts versus observed counts for a predetermined set of probes under a certain dilution criteria for unPurified cDNA Low.
Figure 9:
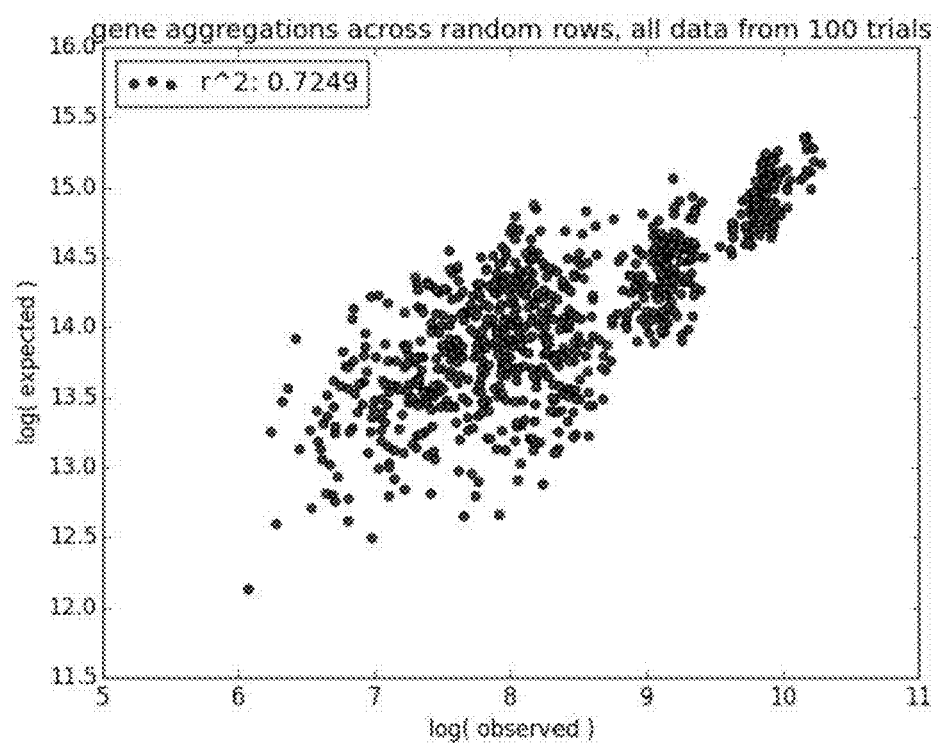
FIG. 9 is a plot illustrating one computational simulation where counts are aggregated across all genes from randomly chosen rows with an $R^2$ value of 0.7249.
Figure 10:
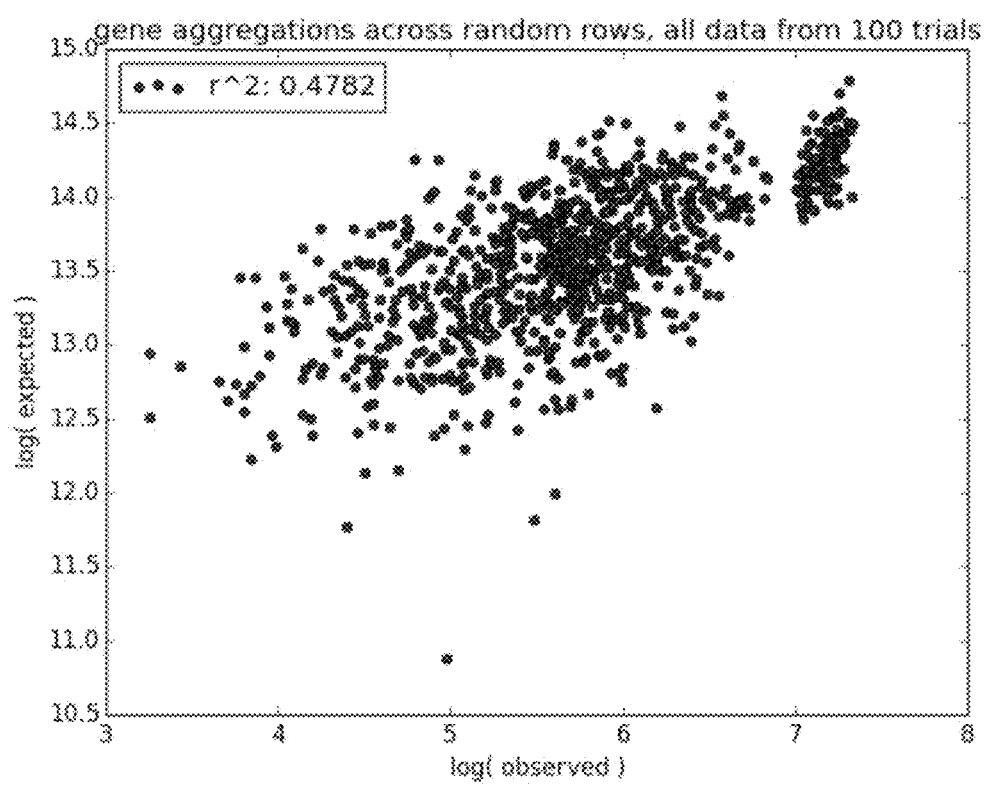
FIG. 10 is a plot illustrating one computational simulation where counts are aggregated across all genes from randomly chosen rows with an $R^2$ value of 0.4728.
Figure 11:
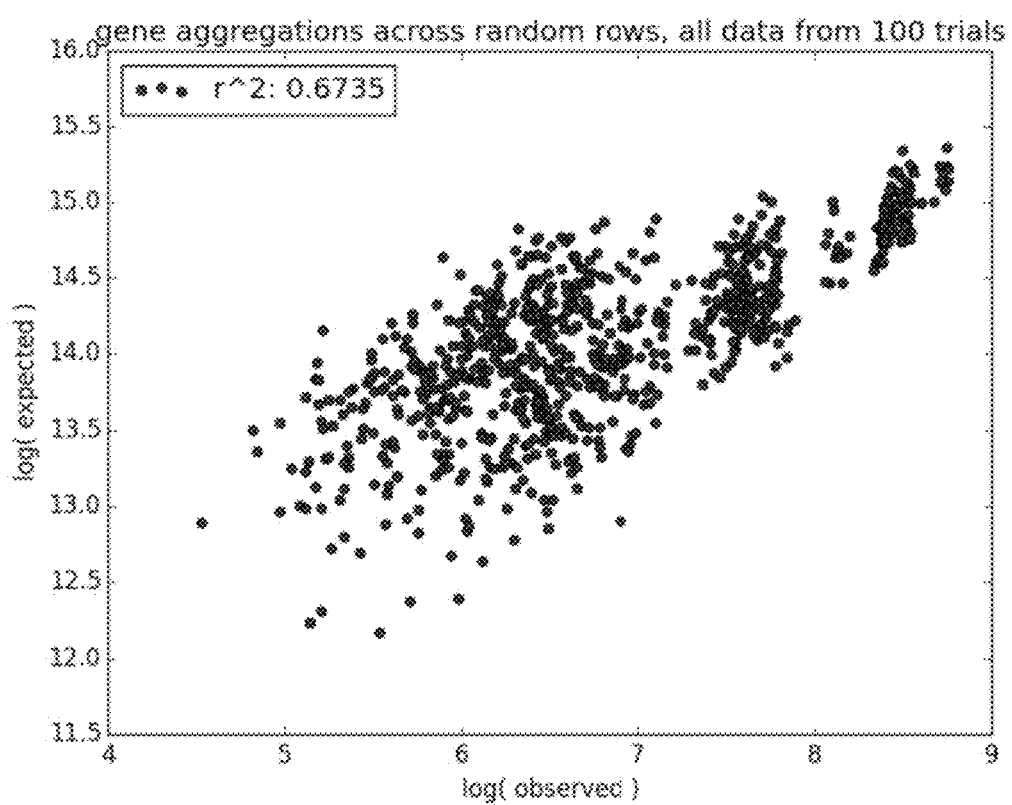
FIG. 11 is a plot illustrating one computational simulation where counts are aggregated across all genes from randomly chosen rows with an $R^2$ value of 0.6735.
Figure 12:
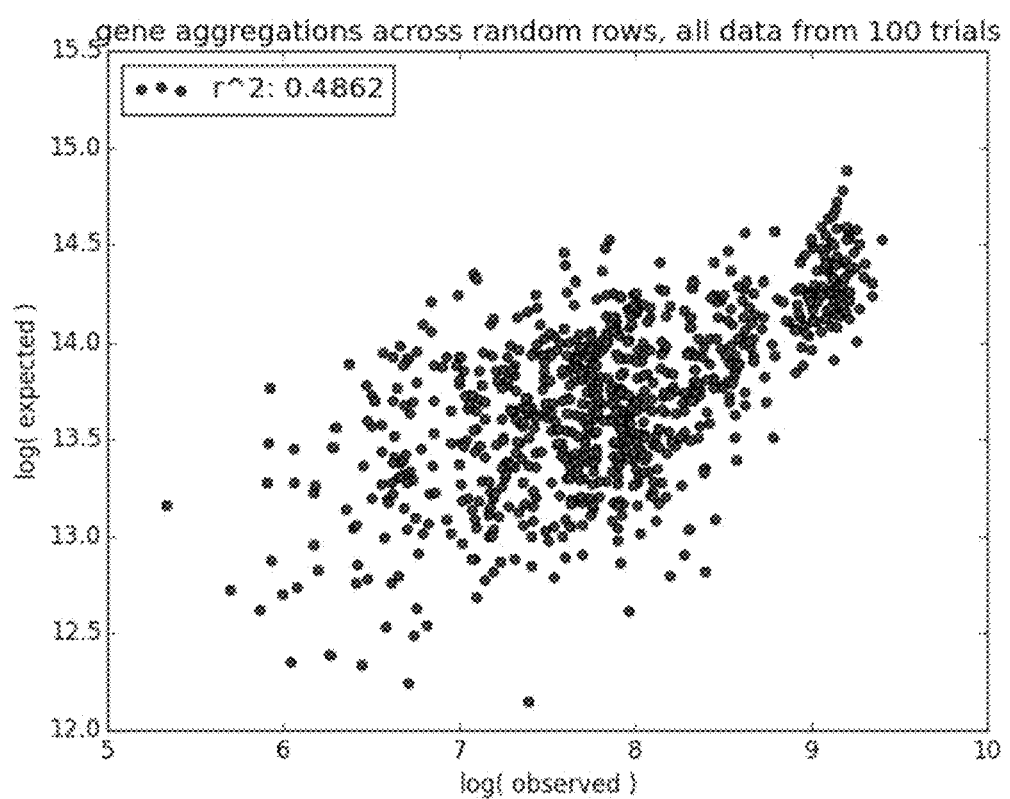
FIG. 12 is a plot illustrating one computational simulation where counts are aggregated across all genes from randomly chosen rows with an $R^2$ value of 0.4862.

FIG. 8 is plot of expected counts versus observed counts for a predetermined set of probes under a range of dilution criteria for unPurified cDNA Low.

The same data can be used to computationally simulate the random setting, where counts are aggregated across all genes from randomly chosen rows, as described above for initial optimizations. Results for these simulations are presented in FIGS. 9-12.

The population of cells with a plurality of genomic sequence or perturbation conditions involves a plurality of cells and perturbations to be tested and measurements sampled to obtain meaningful data and to infer appropriate circuits. The number of genes perturbed, and how many are perturbed simultaneously (the order of the perturbation, pairs, triplets, etc.) varies. In a tissue with n cell types, the rarest present in m %, how many cells X do you need to sequence so that you have at least Y of the rarest subtype.

Figure 15:
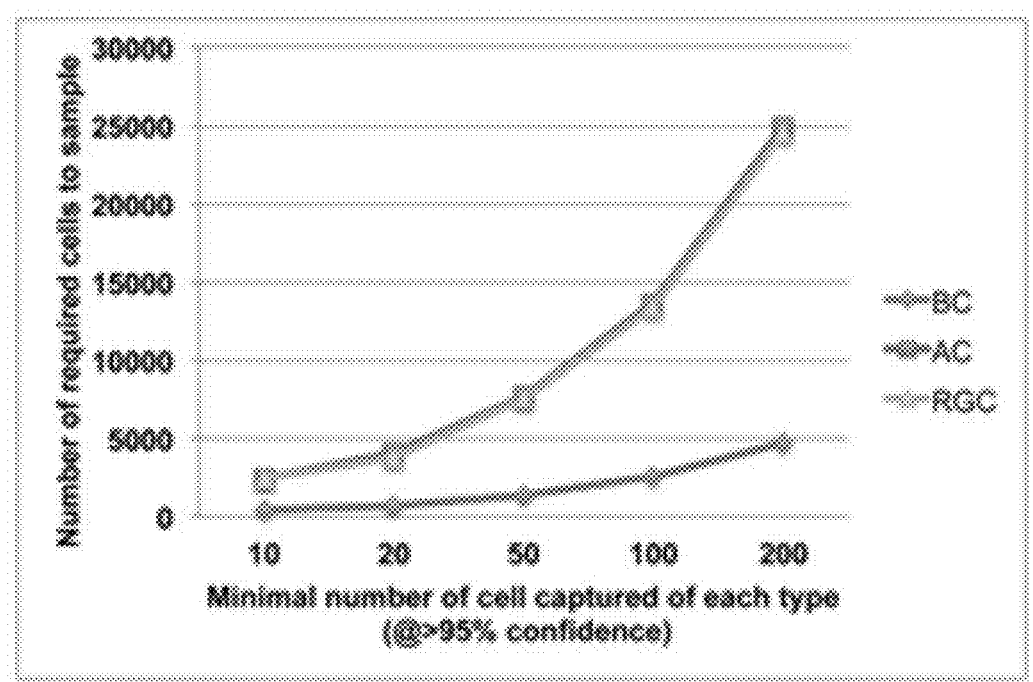
FIG. 15 illustrates an estimate number of cells (Y axis) needed to capture a given minimal number of cells per subtype (X axis) for BCs (rarest subtype ~5%), AC, and RGCs (rarest subtype ~1%).

For example, ~500 cells ensures >95% chance of including >10 of each type, based on the following calculation (FIG. 15). Assume the most conservative scenario that of M cell subtypes (for example, 12), all but one having the lowest predicted proportion (for example, $p_{min}$=5%). Assuming that the Central Limit Theorem holds (a reasonable assumption when solving to detect at least 10 cells of each type) the number of cells of each type i, termed T, will distribute as $E[T_i]=N*p_{min}$, $STDV[T_i]=\approx(N*p_{min}*(1-p_{min}))$. The minimal N (total number of cells to profile) can be solved such that all (m-1) subtypes have at least n cells (the last, majority, subtype easily clears this threshold since its proportion is much higher). Applicants confirmed with simulation that the strategy conservatively holds in practice even for n<10, and take a margin of additional (conservative) error, to allow for subsequent failed RNA-Seq experiments (<20-30%, depending on protocol).

Amplification may involve thermocycling or isothermal amplification (such as through the methods RPA or LAMP). Cross-linking may involve overlap-extension PCR or use of ligase to associate multiple amplification products with each other.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoechst, SYBR gold, ethidium bromide, acridines, proflavine, acridine orange, acriflavine, fluorocoumarin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

Sequencing may be performed on any high-throughput platform with read-length (either single- or paired-end) sufficient to cover both template and cross-linking event UID's. Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem.136:192 (1984); and Elgen and Rigler, Proc. Natl. Acad. Sci. USA 91(13):5740 (1994), all of which are expressly incorporated by reference).

The present invention may be applied to (1) single-cell transcriptomics: cDNA synthesized from mRNA is barcoded and cross-linked during in situ amplification, (2) single-cell proteomics: cDNA or DNA synthesized from RNA- or DNA-tagged antibodies of one or multiple specificities maps the abundance and distributions of different protein-antigens and (3) whole-tissue transcriptomic/proteomic mapping (molecular microscopy or VIPER microscopy): using the frequency of cross-contamination between cells to determine their physical proximity, and via applications (1) single-cell transcriptomics and (2) single-cell proteomics, determining the global spatial distribution of mRNA, protein, or other biomolecules in a biological sample. This may be used, for example, to screen for anti-cancer/pathogen immunoglobulins (by analyzing co-localization of B-cells and T-cells within affected tissue) for immunotherapy. The present invention may also be applied to pooled screening such as pooled CRISPR screens with single-cell transcriptome readout such as that described in Datlinger et al. bioRxiv (2016) dx.doi.org/10.1101/083774.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "variant" should be taken to mean the exhibition of qualities that differ, such as, but not limited to, genetic variations including SNPs, insertion deletion events, and the like.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins DG & Sharp PM (1988), Gene 73(1), 237-244). Once the software has produced an optimal alignment, it is possible to calculate % homology, preferably % sequence identity. The software typically does this as part of the sequence comparison and generates a numerical result.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumarin 151); cyanine dyes; cyanosine; 4',6—diamidino-2-phenylindole (DAPI); 5'5"-dibromopyrogallol-sulfonphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.™. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the non-nucleic acid detectable moiety.

In some embodiments, a detectable oligonucleotide tag may comprise one or more non-oligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag may comprise one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide which may comprise a nucleotide sequence complementary to a capture sequence, e.g. a second detectable oligonucleotide tag. A capture entity may also be any other entity capable of binding to the capture sequence, e.g. an antibody, hapten or peptide. An index sequence is a sequence which may comprise a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium which may comprise computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

The present invention also contemplates multiplex assays. The present invention is especially well suited for multiplex assays. For example, the invention encompasses use of a SureSelect$^{XT}$, SureSelect$^{XT2}$ and SureSelect$^{QXT}$ Target Enrichment System for Illumina Multiplexed Sequencing developed by Agilent Technologies (see, e.g., http://www.agilent.com/genomics/protocolvideos), a SeqCap EZ kit developed by Roche NimbleGen, a TruSeq® Enrichment Kit developed by Illumina and other hybridization-based target enrichment methods and kits that add sample-specific sequence tags either before or after the enrichment step.as well as Illumina HiSeq, MiSeq and NexSeq, Life Technology Ion Torrent. Pacific Biosciences PacBio RSII, Oxford Nanopore MinIon, PromethIon and GridIon and other massively parallel Multiplexed Sequencing Platforms.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Examples

Description of Basic Protocol
Probe Library Generation

Each probe library has two groups of probes. One group is called "left probe," and the other "right probe." Each of the probes bind a short sequence on the target transcript (or cDNA, or target molecule) and the two binding sites are exactly right next to each other (juxtaposition probe set), so that once bound to target they can be ligated to given a single ligation product.

Applicants synthesized the two groups probe separately, and one of the probes will have the measurement barcode, the random molecular index (UMI), and optionally the cell barcodes for single-cell experiments, as shown in FIG. 13.

The probe design in FIG. 13 is just one group of the probe, in the figure it will be the left side probe, given the 5'-3' direction. Applicants generate the probe through performing Klenow extension synthesis followed by lamda exonuclease digestion. In detail, Oligo 1 is first synthesized, containing the Universal adapter, Cell label, UMI, SMRI, and a LK (linker) region, followed by the synthesis of Oligo 2, the complementary sequence.

The left probe combined with the right side probe will be able to bind specifically to the designed location in the target transcript. Applicants then ligate the two probes to form amplification-ready product. This is followed by amplification to add on sequencing adapter. The amplified probes are then purified, quantified, and subjected to next-generation sequencing and analysis, as shown in FIG. 14.

Detailed Experimental Implementation for Bulk RNA
1. Extract RNA from K562 cells (K562 is a human immortalised myelogenous leukemia cell line).
2. Prepare cDNA by synthesis, using the RNA as template.
3. Split part for qPCR and RNA-seq (as a reference control).
4. Split part for probe binding/ligation in the compressive sensing experiment.
5. Synthesize Left and Right Probe and Generate Probe Library Mix
    (1) Synthesize Oligo 1 with the adapter and barcode, and linker region.
    (2) Synthesize Oligo 2 with the complementary sequence to the linker region and gene-specific probe.
    (3) Anneal Oligo 1 and Oligo 2, and perform Klenow extension to synthesize the complete left side probe. The left side of the probe is either purified by column or used directly without further purification.
    (4) Synthesize Oligo 3 with the right side gene-specific probe sequence, and then phosphorylate the right side probe with T4 Polynucleotide Kinase to phosphorylate the 5' end of the oligo to render it ligation-ready.
    (5) Mix probes according to the design matrix to generate a probe library mix with both left and right probe.
6. Hybridize the probe library to the cDNA sample using a slow ramping protocol, where the mix is incubated at 95° C. for 5 minutes, then gradually cooled down to room temperature (25° C.). The annealed mixture containing left and right probes bound to the cDNA molecules are then ligated using Taq ligase to generate the ligation products at 45° C. for 2 hours, and the enzymatic activity is heat-inactivated at 65° C. for 20 minutes.

A control reaction where the probe library mixture is directly ligated with T7 DNA ligase without the addition of cDNA is also performed to obtain the abundance of the probe sets within the library. The ligation step is performed in a similar set-up except cDNA input is substituted with water, and ligation reaction is carried out at room temperature (25° C.) for 2 hours.

7. Amplify the ligation product using the library-amplification primer, which will also add the next-generation sequencer adapter to complete sequencing-ready library construction. The amplified is purified and size-selected between 200-300 bp and quantified.

Experimental Design for Implementation for Single Cell Sample

Each cell is captured and encapsulated in hydrogel droplet, which contains one side of the probe. These single-cell containing droplets are then lysed to allow initial hybridization, barcoded uniquely. Then, the other side of the probe will be added to the system to allow hybridization, ligation, and amplification. The final products are then purified and sequenced (or quantified/detected in other means), and subject to data analysis.

Composite Measurements can be Made by Multiplexed Direct RNA Probing

Below, the Applicants present a proof-of-concept for composite measurements of mRNA levels based on probe hybridization and qPCR.

For each measurement, the Applicants pre-selected and synthesized a set of paired ssDNA probes that have two components: gene-specific parts that hybridize to two adjacent sequences on the RNA transcript of target genes, and a measurement-specific barcode that is common to all probe-sets belonging to the same measurement. Prior to hybridization, the concentrations of probes targeting each gene were adjusted according to their compositional weights. The probe libraries for each measurement were then hybridized to an RNA sample in a pooled fashion. The total abundance of hybridized probes sharing a common measurement barcode in a single readout was quantified by ligation-mediated amplification: Pairs of ssDNA probes that have hybridized immediately adjacent to each other were ligated with an enzyme that selects for RNA-DNA hybrids, and m independent qPCR reactions were then performed, each with a primer pair specific to a given measurement barcode. The net abundancy (i,j) (may correspond to a coefficient of matrix M) determined from qPCR reaction i in sample j, therefore, ideally corresponds to the product:

$$y\_(i,j) = a\_i \, x\_j$$

where a_i, a vector with one entry per gene, corresponds to the composition (or concentration) of probes targeting each gene in the library and may correspond to a column or line of matrix DM, and x_j represents the abundance of each gene in the sample and may correspond to a column or line of matrix S. That is, the qPCR reaction is designed to read out the dot product, or the sum of probe concentrations multiplied by their target gene abundances. In some cases the compositional weights will correspond to negative numbers. The Applicants addressed this by doubling the number of measurement barcodes, so that for each measurement i there was one qPCR reaction (î+) containing all probes for genes with positive compositional weights, and a second qPCR reaction (î−) containing all probes for genes with negative weights. We then take y_(i,j) to be the difference y_(î+,j)−y_(î−,j).

There are several key advantages to the exemplified workflow: First, since the quantities y_(i,j) are sufficient to recover the gene expression levels according to the results presented above, ideally generating costly intermediate measurements will be avoided, such as the specific contribution of a given gene to a given measurement. The qPCR readout reflects the net abundance of ligated probe pairs from all genes sharing a common barcode to directly yield these results. Second, directly probing RNA avoids the possible biases introduced during reverse transcription and whole-transcriptome amplification, while also simplifying the workflow. In addition, since the Applicants directly probe RNA and are not reliant on, for example, 3' poly-A capture of transcripts, the Applicants can target each transcript in multiple locations, which is expected to increase the probability of sampling any given transcript. These latter advantages are likely to be particularly important in the single cell context.

Using RNA prepared from K562 cells, the Applicants evaluated this experimental setup on a subset of 24 genes. These genes were selected randomly to capture a large dynamic range of abundance, from the highly abundant housekeeping genes (ACTB) to very lowly expressed ones (EMR1). Single probes for each gene were first evaluated, using approximately 100 cellular equivalents of RNA. Gene expression levels based on the present barcoded, ligation-mediated amplification were compared with abundance measures derived from standard qPCR experiments. Under a series of dilutions of each probe pair (across 1000x, or three order of magnitude total range), the measured correlations varied from 13% to 64%. The Applicants next combined 4 different probe pairs for each gene with the same given common index, and observed an increase in correlations (ranging from 39% to 96%) across the same range of dilutions. This increase is likely due to robustness conferred by averaging probes with uncorrelated noise, and by potential repeated sampling of a transcript at multiple locations. Finally, the Applicants designed 20 arbitrary sets of composite measurements by random linear combinations of the 24 genes, and created the corresponding probe libraries. With two replicates of these libraries using different measurement barcodes the Applicants observed 85% and 90% correlation with expected values calculated from the same linear combinations of known gene abundances. This demonstrates that composite measurements (either across locations in a gene, or across genes) are more robust to noise, and more generally demonstrates the accuracy and robustness of the workflow disclosed herein for implementing a key step in molecular compressed sensing.

All publications, patents, and patent applications mentioned herein are incorporated by reference to the same extent as if each individual publication, patent or patent application was specifically and individually indicated to be incorporated by reference in its entirety.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of measuring relative abundances of n biomolecules in a pool of samples, comprising:
   a) generating a Design Matrix comprising m×n relative measurement values, where m is a number of types of measurement vectors and n is a relative number of types of biomolecules;
   b) generating a probe library corresponding to the Design Matrix, wherein the probe library comprises a collection of molecules assembled according to the types of measurement values m, where each molecule has a tag for one of the measurement vectors operably linked to a probe for one of the types of biomolecules and an amount of a specific probe is known relative to an amount of the other probes based on the Design Matrix;

c) contacting the probe library to the pool of samples, resulting in m measurement results for each sample of the pool of samples;

d) generating an Observed Measurement Matrix M comprising m×c measurement results, where m is a number of types of measurement vectors and c is a number of observed types of biomolecules for each sample in the pool of samples; and e) determining the relative abundance of the biomolecules in each of the samples by applying a sparse coding solving process comprising matrix factorization to the Observed Measurement Matrix M and the Design Matrix to determine system matrix S comprising n×c results, wherein n is the relative number of types of biomolecules and c is the number of observed types of biomolecules for each sample in the pool of samples.

2. The method of claim 1, wherein the measurement values of the Design Matrix generated are independent or random.

3. The method of claim 1, wherein contacting the probe library comprises binding or hybridizing.

4. The method of claim 1, wherein the biomolecules are transcripts, proteins, DNAs, non-naturally occurring nucleic acids, or peptides.

5. The method of claim 1, wherein the samples are cells, blood, hair, nails, mucus, tissue, feces, or urine samples.

6. The method of claim 1, wherein each molecule in the probe library further comprises a tag for one of the samples.

7. The method of claim 1, further comprising adjusting the Design Matrix according to a basis, wherein the basis is a collection of vectors that form a set that is linearly independent and that spans a vector space of the collection of vectors.

8. The method of claim 1, wherein generating the Observed Measurement Matrix M comprises hybrid selection and tag quantification.

9. The method of claim 8, wherein the tag quantification comprises sequencing.

10. The method of claim 1, wherein the probe is a molecule that binds to the biomolecule, or a complex of molecules.

11. The method of claim 1, wherein the sparse coding solving process is applied to noisy compositional observations within the Observed Measurement Matrix.

12. The method of claim 1, wherein the sparse coding solving process further comprises matrix factorization of a module dictionary matrix X comprising a dictionary of expression modules wherein each column is a vector of length n and is one element of the dictionary and a module activity level matrix B comprising an x n matrix whose individual columns describe a linear combination of columns from X to determine S.

13. The method of claim 12, wherein the matrix factorization comprises one or more of the following:
setting number of modules active in any sample lower than 500;
setting number of genes in any module greater than 5 and lower than 25,000 and the number of modules in which each gene participates is at least one;
setting total number of modules is between one tenth and five times the number of samples.

14. The method of claim 12, wherein the matrix factorization comprises non-negative matrix factorization (NMF).

15. The method of claim 12, wherein the matrix factorization comprises sparse module activity factorization (SMAF), and wherein the module dictionary matrix X only comprises non-negative entries, wherein the entries represent membership in a module.

16. The method of claim 12, wherein the sparse coding solving process is applied to training data corresponding to a fraction of information contained in the Observed Measurement Matrix to create a training system matrix S to learn the module dictionary matrix X.

17. The method of claim 1, wherein the sparse coding solving process comprises blind compressed sensing (BCS) to learn the system matrix S.

* * * * *